United States Patent
Summit et al.

(10) Patent No.: US 9,782,274 B2
(45) Date of Patent: *Oct. 10, 2017

(54) METHOD FOR CREATING A DESIGN FOR A REPLACEABLE FAIRING

(71) Applicant: 3D Systems, Inc., Rock Hill, SC (US)

(72) Inventors: Scott Summit, Mill Valley, CA (US); Kenneth B Trauner, San Francisco, CA (US)

(73) Assignee: 3D Systems, Inc., Rock Hill, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/854,731

(22) Filed: Apr. 1, 2013

(65) Prior Publication Data
US 2013/0226533 A1    Aug. 29, 2013

Related U.S. Application Data

(63) Continuation of application No. 12/881,419, filed on Sep. 14, 2010, now Pat. No. 8,417,487, which is a continuation-in-part of application No. 11/973,069, filed on Oct. 5, 2007, now Pat. No. 7,797,072, and a
(Continued)

(51) Int. Cl.
| | |
|---|---|
| *G06F 17/50* | (2006.01) |
| *A61F 2/50* | (2006.01) |
| *B33Y 50/00* | (2015.01) |
| *G06F 19/00* | (2011.01) |

(Continued)

(52) U.S. Cl.
CPC ............ *A61F 2/5046* (2013.01); *B33Y 50/00* (2014.12); *G06F 19/3437* (2013.01); *G06T 19/00* (2013.01); *A61F 2002/5001* (2013.01); *A61F 2002/505* (2013.01); *B33Y 80/00* (2014.12); *G06T 2210/41* (2013.01)

(58) Field of Classification Search
CPC ............ G06F 19/3437; G06T 2210/41; A61F 2002/5001
USPC ...................................................... 703/1, 6, 11
See application file for complete search history.

(56) References Cited

U.S. PATENT DOCUMENTS

| | | |
|---|---|---|
| 2,318,864 A | 2/1940 | Jackson |
| 2,980,110 A | 4/1961 | Brumfield et al. |
| 3,093,131 A | 6/1963 | Kashyap |
| (Continued) | | |

FOREIGN PATENT DOCUMENTS

| | | |
|---|---|---|
| JP | H111999318962 | 11/1999 |
| JP | 2000-502584 | 3/2000 |
| (Continued) | | |

OTHER PUBLICATIONS

English Translation at China's Second Office Action for Chinese Application No. 200980144730 dated Aug. 12, 2013 (3 pages).
(Continued)

*Primary Examiner* — Aniss Chad
(74) *Attorney, Agent, or Firm* — Staniford Tomita LLP

(57) ABSTRACT

A fairing can be attached to a prosthetic limb or over a brace to alter the appearance of the prosthetic limb or brace. The outer surface of the prosthetic limb can be a mirror image of an intact limb and the outer surface of the brace can have an outer surface that corresponds to an injured limb. Because the fairing fits closely around the prosthetic limb or brace, the interior surface of the fairing has a surface that corresponds to a mirror image of an intact limb or an outer surface of an injured limb.

20 Claims, 16 Drawing Sheets

Related U.S. Application Data continuation-in-part of application No. 12/615,196, filed on Nov. 9, 2009, now Pat. No. 8,005,651.

(51) Int. Cl.
*G06T 19/00* (2011.01)
*B33Y 80/00* (2015.01)

(56) References Cited

U.S. PATENT DOCUMENTS

| | | | |
|---|---|---|---|
| 3,953,900 | A | 5/1976 | Thompson |
| 4,776,327 | A | 10/1988 | Russell |
| 4,807,605 | A | 2/1989 | Mattingly |
| 4,827,916 | A | 5/1989 | Kosova |
| 5,443,510 | A | 8/1995 | Shetty et al. |
| 5,662,594 | A | 9/1997 | Rosenblatt |
| 5,713,837 | A | 2/1998 | Grim et al. |
| 5,741,215 | A | 4/1998 | D'Urso |
| 5,768,134 | A | 6/1998 | Swaelens et al. |
| 5,857,987 | A | 1/1999 | Habermeyer |
| 5,880,964 | A | 3/1999 | Schall et al. |
| 5,888,216 | A | 3/1999 | Haberman |
| 6,427,695 | B1 | 8/2002 | Zanetti et al. |
| 6,540,708 | B1 | 4/2003 | Manspeizer |
| 6,572,571 | B2 | 6/2003 | Lowe |
| 6,597,965 | B2 | 7/2003 | Graves et al. |
| 6,613,006 | B1 | 9/2003 | Asherman |
| 6,725,118 | B1 | 4/2004 | Fried et al. |
| 6,726,641 | B2 | 4/2004 | Chiang et al. |
| 6,968,246 | B2 | 11/2005 | Watson et al. |
| 7,058,471 | B2 | 6/2006 | Watanabe |
| 7,127,101 | B2 | 10/2006 | Littlefield et al. |
| 7,210,926 | B2 | 5/2007 | Tadros et al. |
| 7,242,798 | B2 | 7/2007 | Littlefield et al. |
| 7,340,316 | B2 | 3/2008 | Spaeth et al. |
| 7,896,827 | B2 | 3/2011 | Ingimundarson et al. |
| 8,005,651 | B2 | 8/2011 | Summit et al. |
| 2002/0016631 | A1 | 2/2002 | Marchitto et al. |
| 2002/0026135 | A1 | 2/2002 | Lowe |
| 2003/0032906 | A1 | 2/2003 | Narula |
| 2003/0065259 | A1 | 4/2003 | Gateno et al. |
| 2003/0137510 | A1* | 7/2003 | Massen .................. 345/420 |
| 2004/0019266 | A1 | 1/2004 | Marciante et al. |
| 2004/0054311 | A1* | 3/2004 | Sterling ............... A61F 5/0123 602/26 |
| 2004/0068337 | A1 | 4/2004 | Watson et al. |
| 2004/0162511 | A1 | 8/2004 | Barberio |
| 2004/0230149 | A1 | 11/2004 | Littlefield et al. |
| 2004/0236424 | A1 | 11/2004 | Berez et al. |
| 2004/0260402 | A1 | 12/2004 | Baldini et al. |
| 2005/0015172 | A1 | 1/2005 | Fried et al. |
| 2005/0043835 | A1 | 2/2005 | Christensen |
| 2005/0061332 | A1 | 3/2005 | Greenawalt et al. |
| 2005/0065458 | A1 | 3/2005 | Kim |
| 2006/0161267 | A1 | 7/2006 | Clausen |
| 2007/0016323 | A1 | 1/2007 | Fried |
| 2007/0225630 | A1 | 9/2007 | Wyatt et al. |
| 2007/0288198 | A1* | 12/2007 | Massen et al. ............... 702/167 |
| 2008/0120756 | A1 | 5/2008 | Shephard |
| 2008/0294083 | A1 | 11/2008 | Chang et al. |
| 2008/0319362 | A1 | 12/2008 | Joseph |
| 2009/0254015 | A1 | 10/2009 | Segal et al. |
| 2010/0137770 | A1 | 6/2010 | Ingimundarson et al. |
| 2010/0138193 | A1 | 6/2010 | Summit |

FOREIGN PATENT DOCUMENTS

| | | |
|---|---|---|
| JP | 2000-592584 | 3/2000 |
| JP | 2006-513482 | 4/2006 |
| JP | 2007068855 | 3/2007 |
| WO | 97/24085 | 7/1997 |
| WO | 2010/054341 | 5/2010 |
| WO | 2010-054341 | 5/2010 |
| WO | 2010/099130 | 9/2010 |

OTHER PUBLICATIONS

English Translation of China's First Office Action for Chinese Application No. 200980144730.6 dated Nov. 28, 2012 (6 pages).
International Search Report and Written Opinion for PCT Application No. PCT/US2010/055793, International Filing Date: Nov. 8, 2010 (Nov. 8, 2010).
International Search Report and Written Option, dated Oct. 28, 2011, PCT/US11/141515.
English Translation of China's First Office Action Chinese Application No. 201180040807.2 dated May 12, 2014 (8 pages).
English Translation of China's First Office Action for Chinese Application No. 201080060735.3 dated Apr. 1, 2014 (5 pages).
English Translation of Japan's First Offire Action for Japanese Application No. 2012-538866 dated Jun. 6, 2014 (3 pages).
English translation of China's Second Office Action dated Mar. 20, 2015 (7 pages).
English translation of Japan's First Office Action dated Mar. 24, 2015 (3 pages).
English translation of Korea's Second Office Action for Korea Patent Application No. 10-2014-7003756 (4 pages).
English translation of Chinese First Office Action for Chinese Patent Application No. 201280040486.0 dated Mar. 9, 2015 (5 pages).
English translation of Chinese Third Office Action for Chinese Patent Application No. 201080060735.3 dated Aug. 4, 2015 (3 pages).
Canadian Office Action for Canadian Patent Application No. 2740797 dater Aug. 31, 2015 (3 pages).
European Search Report for European Patent Application No. 12825770.6 dated Sep. 3, 2015 (10 pages).
English translation of KIPO's Notice of Preliminary Rejection for Korea Patent Application No. 10-2011-7013219 (3 pages).

* cited by examiner

METHOD FOR CREATING A DESIGN FOR A REPLACEABLE FAIRING

CROSS REFERENCE TO RELATED APPLICATIONS

This application is a continuation of U.S. patent application Ser. No. 12/881,419, "Replaceable Fairing For Prosthetic Limb Or Brace" filed Sep. 14, 2010 which is now U.S. Pat. No. 8,417,487 which is a continuation in part of U.S. patent application Ser. No. 11/973,069, "Prosthetic Limb With Replaceable Fairing" filed Oct. 5, 2007 which is now U.S. Pat. No. 7,797,072 and a continuation in part of U.S. patent application Ser. No. 12/615,196, "Custom Braces, Casts And Devices And Methods For Designing And Fabricating" filed Nov. 9, 2009 which is now U.S. Pat. No. 8,005,651. U.S. Pat. Nos. 8,417,487, 8,005,651 and 7,797,072 are hereby incorporated by reference in their entirety.

BACKGROUND

A prosthesis limb replaces a missing extremity, such as an arm or a leg and may be needed for a variety of reasons, including diseases and accidents. An artificial limb may also be needed when a person is born with a missing or damaged limb(s). The type of prosthesis limb used is determined largely by the extent of an amputation or loss and location of the missing limb. A transtibial prosthesis is an artificial leg that is attached to a user below the knee and includes a lower leg, ankle and foot. The transfemoral prosthesis is an artificial leg that is attached to the user's amputated limb above the knee and includes an upper leg and mechanical knee. A transradial prosthesis is an artificial arm that is attached to the user below the elbow and includes a forearm and hand. A transhumeral prosthesis is an artificial arm that is attached to the user above the elbow.

In developing areas of the world, including large portions of Africa, the leading causes of amputations are industrial, vehicular, and war related accidents. In more developed areas, such as North America and Europe, the leading causes for the amputations are diseases including cancer, infection and circulatory. In the United States, approximately 100,000 legs are lost each year to diabetes, vascular disorder, accidents and cancer. Because there are so many amputations, there is a substantial need for prosthetic limbs.

The engineering of prosthetic limbs has improved greatly. In particular, artificial knees and feet have been developed for prosthetic legs that provide increased mobility and functionality. While the engineering and mechanics of prosthetic limbs have evolved greatly, very little thought has been given to the aesthetics of the human being for whom the device was intended. With reference to FIG. 1, a modern prosthetic leg 102 is shown having a socket 122 that has a recessed surface that engages the end of the user's amputated leg. The socket 122 is typically a padded plastic structure that distributes the compression forces on the end of the amputated limb. The bottom of the socket 122 is attached to a pylon 124 which is a tubular support that can be made of titanium or aluminum. The pylon can be manufactured through an extrusion process. The bottom of the pylon 124 is attached to an artificial foot 126 that can be a molded plastic structure. The prosthetic leg 102 may also have a foam covering 128 and can be attached to the socket 122 and pylon 124 to provide a more uniform shape. The various socket 122, pylon 124 and foot 126 can be coupled together using fasteners including bolts, screws and adhesives.

A problem with the existing prosthetics is that they neglect the fundamental symmetry of the human form. Symmetry is a visible indication of the health of the individual and asymmetry can be perceived as a health shortcoming. Many medical conditions such as a nervous tick, stroke, leprosy, elephantitis, etc. are exhibited in patients as an asymmetric appearance. Similarly, the asymmetric nature of existing prosthetic limbs communicates that a user has a 'medical necessity' and reinforces a message that the wearer is damaged or defective.

For many amputees the asymmetric appearance of the prosthetic limb is more troublesome than their physical discomfort. The task of disguising the asymmetric appearance of the prosthetic limb is nearly impossible because the socket 121, pylon 123 and foot 125 used to create the prosthetic limb are a collection of parts from a variety of manufacturers. Because the socket 121 and pylon 123 are not specifically designed for left or right sides of the body, the components cannot have a symmetric appearance. Efforts to improve the appearance with a flesh-colored electrometric foam cover 127 are also problematic. While the diameter of the cross section may be more uniform than the socket 121, pylon 123 and foot 125, the cover 127 is not an accurate dimensional representation of a human leg. The simulated human flesh is typically not life like and can connote dead tissue.

Similarly, braces are typically designed to support and protect an injured limb but not provide any sort of symmetric appearance. There are various types of braces that are used to support and protect a portion of a body during recovery. Braces are used to limit the movement of a joint and are useful in preventing injury or allowing a joint to heal by preventing movement in the injury direction. Braces can be elastic and may be made of stretch materials or hinged which include some hard components. Elastic braces are frequently made from woven materials such as cotton, lycra, nylon or other blends that provide exceptional breathability and wearing comfort. These braces conform to the elbow, wrist, leg and knee providing a natural freedom of movement.

What is needed is an improved prosthetic limb and brace that is symmetrical in form and also allows the user to change and personalize the appearance.

SUMMARY OF THE INVENTION

The present invention is directed towards an improved prosthetic limb and brace that can also include a removable fairing that allows the user to personalize and change the appearance of the limb or brace. The prosthetic limb and fairing are created by a prosthetic designer using computer aided design (CAD) software and computer controlled fabrication processes. While the prosthetic limb is described as a leg, the same processes can be used to fabricate prosthetic arms, and as such, prosthetic arms are intended to fall within the scope of the present invention. In addition to prosthetic arms, braces including, foot, leg, arm, hand and back braces are intended to fall within the scope of the present invention.

The prosthetic designer first creates a virtual limb and fairing using a computer aided design system. The design of the prosthetic leg can include a socket, upper leg, knee, lower leg, and foot. If the user has an intact leg, a prosthetic leg having a matching outer surface can be designed. In order to accurately create a matching prosthetic leg, the surface of the user's intact leg is first measured. The measurement of the intact leg is preferable done with an optical measuring device. In a preferred embodiment a photogrammetry process is used in which the surface data for a patient is obtained from a plurality of photographs of the patient. In order to accurately measure the surface of the patient, reference points can be applied to the patient's skin in various different ways. For example photogrammetry or laser scanning.

In a preferred embodiment a photogrammetry process is used in which the surface data for a patient is obtained from a plurality of photographs of the patient. In order to accurately measure the surface of the patient, reference points can be applied to the patient's skin in various different ways. The surface should have at least twelve well distributed reference points visible in each photograph and at least twenty reference points for an entire surface of an object. More reference points will result in a more accurate measurement of the object. The marks can be dots formed by ink, pencil, crayon, grease, graphite, tape, stickers, or other markings placed directly on the patient or on a form fitting cover such as a stockinette worn by the patient. In an embodiment, the cloth of the form fitting covering can be printed with the dots, textured pads or a grid of intersecting lines so that the patient will have a set of reference points as soon as the covering is worn by the patient. In yet another embodiment, a light projector can be used to project a pattern of light onto the patient. The pattern of light can be an array of spot points, a grid of intersecting lines or any other pattern that allows images of points on the patient to be detected. The light on the patient serves as the markings can be white or colored light markers that are projected onto the patient with a projector. Multiple projectors or mirrors may be necessary to project the light onto all required surfaces of the patient.

In addition to reference points for obtaining the surface contours of the patient's body surface, the doctor or practitioner can also mark areas of the patient's body to indicate the location of other features of the brace. For example, markings can indicate the end edge(s) of the brace, padding areas, boney prominences, sensitive areas of the skin, holes, windows, pathologic sites (fracture or surgical site localization), underlying anatomy (ex spinous processes and spine alignment) recessed areas where the brace should not be made precisely to the contour of the patient and other features to be formed in the brace. The markings can be made directly on the patient or on the form fitting cover worn by the patient. Like the reference points, the additional markings can be ink, ink, pencil, crayon, grease, graphite, tape, stickers, or other markings and must provide a clear visual contrast. The markings can be coded by color or in another manner to indicate the type of feature to be formed at the markings. The different codings can also be used to indicate the degree or amount of deformation in an identified region, type of window, or other brace feature. The markings can be a three dimensional object(s) that provide additional information. For example, a rod, an arrow or other object marker can indicate an axis of rotation of a joint or other features.

After the patient has been marked, the portion of the patient's body that is in need of a cast or brace is placed in front of one or more still or video cameras. The cameras can face one or more sides of the patient's body and can be spaced apart from each other by a known distance. In some embodiments, a set of cameras can be arranged around the patient so that a complete set of still images or photographs of the body around a circumference can be taken. In a preferred embodiment, the cameras are arranged in groups of two cameras. The two cameras can be mounted on a bracket that spaces the cameras apart from each other. The two cameras are aimed in the same general direction towards the patient or limb of the patient but offset by an angle. In a preferred embodiment, the camera lenses can be parallel to each other in a first plane and angled towards each other in a second plane. The separation and angle allow the two cameras to each take a picture that includes the same portions of the patient's body but from slightly different angles. The reference points on the body are triangulated from the pictures to obtain the surface contours. If photographs around the entire patient are needed, three or four groups of cameras can be arranged around and directed towards the patient. The cameras can be coupled to a single switch which causes all of the cameras to be actuated simultaneously. The cameras can also be coupled to a flash mechanism. The flash for one camera can be triggered by the shutter of one camera being actuated. The other cameras aimed at the patient can include light sensors which cause their shutters to actuate in response to the flash of light. Thus, the actuation of the first camera will immediately cause all other cameras to be actuated. Since all pictures are taken in a fraction of a second, the body can be placed in front or between the cameras and there is normally no need to immobilize the patient or hold the body or limb still for an extended period of time.

This fast image capture feature is particularly important for pediatric or veterinary medical devices such as pediatric spica casts or veterinary braces. It can be very difficult to keep an infant or an animal steady for other types of scanning processes. For most children and animals casting and bracing is a traumatic experience associated with significant pain and morbidity. Both application and removal of casts and braces is associated with discomfort. For many applications the children and animals require either sedation or anesthesia for application of the casts. For example, hip spica casts most frequently are applied with the patient in an induced sleep in the operating room.

Capturing a three dimensional image of a child's anatomy requires that the child be held immobile during the duration of the scan. Otherwise the child would require sedation. For most pediatric applications, only photogrammetry will offer near instantaneous three dimensional image capture. Combining with markings and photogrammetry, children can undergo virtual fittings for braces while minimizing the need for sedation or anesthesia and reducing the trauma of the experience. Because many infants have a substantial amount of baby fat, the marking of the infant may be the most efficient means for identifying the locations of the underlying anatomy. Common applications for this technology include but are not limited to: pediatric spica casts, Pavlik brace, clubfoot casting, metartus adductus casting, Blounts disease casting/bracing, ankle foot orthosis, pediatric ankle casts, pediatric walking casts, spine-TLSO braces, halo body cast, cervical collar, torticollis bracing and other medical devices. By obtaining data from images, there is no need to keep the infant or animal still for an extended period of time.

In another embodiment, a single 3-D camera can simultaneously capture multiple off axis images via a single camera. The single camera may capture multiple images on a single frame of film. The multiple images can be used to capture the 3-D image. It is also possible to take multiple images of a patient with a single camera that is moved around the patient to capture multiple images at different angles if the patient remains very still. A single camera can also be coupled to a lens system that can capture images of the patient from suitable angles and positions.

In order to get an accurate surface position, each of the reference points on the body must be visible in two or more photographs or images. The images are analyzed by a computer surface reconstruction program. The program triangulates the reference points through photogrammetry also known as digital image correlation to determine a surface geometry of the body. In addition to the reference points, additional features of the device as marked on the patient are also shown in the images and visible to the CAD program operator. The features can include edges of the brace or device, holes, pads, windows, hinges, different materials and other features. The system operator or the CAD software can identify the features and add the features at the marked locations on the brace or device. Frequently when a brace or cast is needed, the patient is suffering from some internal injuries and additional information such as MRIs or X-rays are available. In an embodiment, the photogrammetry can be combined with the MRI or X-ray data to identify the locations or regions that need to be accessible or the locations of bones that are sensitive to abrasion. By integrating the MRI and/or X-ray data, the device can be made more accurately. The use of data from the other modalities is especially useful in identifying the axis of rotation of the joint accurately in all planes to render a more accurate range of motion brace.

In other embodiments, a laser measuring device can be used to scan the intact leg and obtain measurements for surface points across the entire leg that is a digital representation of the outer surface. Laser scanners that are suitable for scanning the leg are available from Polhemus, HandiScan 3D and Thinglab. Alternatively, the leg can be measured through other means. The digital scan data can then be converted into surface that can be used by the CAD system. This scan data conversion software is available from GeoMagic. A digital representation of the intact leg surface can then be manipulated by the CAD software to create a mirror image of the intact limb that will be used as the outer surface data for the prosthetic limb. The prosthetic designer can use the CAD software to join the mirror image surface to the other components of the prosthetic leg and display the assembled prosthetic leg. Suitable CAD software for prosthetic and fairing design is available from Pro/Engineer. As discussed in the background, for aesthetic and emotional reasons, it is important that the prosthetic limb have a symmetric appearance to the intact leg.

The socket shape must correspond very closely to the end of the amputated limb in order for the prosthetic leg to be comfortable when worn. The socket design data is typically provided by a prosthetist. Like the leg surface data, the socket design data can be obtained through optical scanning of the end of the amputated limb. Alternatively, the end of the amputated limb can be measured manually with various mechanical measuring devices. These measurements are used to create a socket surface shape that is substantially the reversed shape of the end of the amputated limb. The socket design may also factor in padding materials that are placed between the amputated limb and the socket wall.

In addition to the mirror image intact limb data and the socket data, the prosthetic leg requires a foot. In an embodiment, feet are stock items that are manufactured in various sizes and models. Some feet have energy-storing members that allow the user to run more efficiently. Alternatively, the feet can be sized to match the intact foot. Digital representations of the stock feet can be stored in a database that is accessible to the design system. Alternatively, foot data can be obtained by creating mirror image data of the user's intact foot through a laser scanning process as described above.

The prosthetic designer uses the CAD system to combine the leg surface data with socket and foot data to create a complete virtual prosthetic leg that is displayed on the computer. The GUI can allow the prosthetic leg components to be easily changed using integrated design tools. These GUI controls can allow the prosthetic designer to alter the prosthetic design in various ways. A GUI tool can be used to change the foot used with the leg. The GUI tool can also be used to modify the leg to include specific colors, textures and surface features. Thus, the user can create a prosthetic leg that is substantially a mirror image to the intact leg or create a leg that is very different in appearance.

In an embodiment, the prosthetic leg or brace can also include a fairing that is a removable layer that covers a portion of the prosthetic leg or brace. The fairings can be removed or replaced so the user can alter the appearance of a portion of the prosthetic leg or brace. The fairing can be easily changed as desired by the user. The CAD system can also allow the prosthetic designer to view the prosthetic leg or brace with various fairing designs. For example, the GUI can include a fairing material controller that allows the user to see many virtual fairings made from a variety of materials including: metals, plastics, fabrics, leather, etc. The prosthetic designer can also use the CAD system to select the attachment mechanism for the fairing. The attachment mechanism can include adhesives, fasteners, magnets, etc. The fairing must be securely attached to the prosthetic leg or brace to remain attached during normal physical activities. The CAD system is particularly useful because it allows the user to design and view any desired combination of features and fairings prior to fabrication.

In addition to the physical appearance, the prosthetic leg or brace must also be strong enough for the required use. A prosthetic leg must be able to support the user's weight and impact while running or jumping and a prosthetic arm must be able to withstand the normal use forces. In an embodiment, the strength of the prosthetic limb can be provided by internal structures such as a load-bearing pylon. An outer surface that is not load bearing can be attached around the load-bearing pylon. In order to create a lighter structure, void space can exist between the pylon and the outer surface. In other embodiments, the limb is fabricated with the outer surface functioning as a load-bearing member. Similarly, the brace must provide enough physical strength to properly support the injured limb. Because the materials used to fabricate the prosthetic limbs and braces are very strong, the system can design an external surface that is a thin wall. The prosthetic limb can possibly include an internal structure that adequately supports the expected loads and the outer surface wall.

The CAD system can be used to design the load-bearing member of the prosthetic leg. The prosthetic designer can input the weight and activity level of the user into the CAD system and the required strength can then calculate based upon expected loads. The CAD system can then design a load-bearing structure that will be able to support the load requirements. As discussed above, the load bearing member can be an internal elongated structure that supports the entire load or alternatively, an integrated design in which the entire structure is load bearing. The CAD system can be used to design a load-bearing structure that has the required strength for both the internal load-bearing or integrated configurations.

The CAD system can also provide information to the prosthetic designer that may be important to the prosthetic leg design. For example, the weight of the prosthetic leg will vary depending upon the required strength, the volume of material needed and the density of the material. Once the design is completed, the volume of material and weight can be determined. The weight of a fairing can similarly be determined based upon the volume of the design and materials selected by the user. The system can display the estimated weights for the leg or brace and fairings during the design process. The prosthetic designer can determine if the weight is suitable for the user. If the weight is too heavy, the design of the prosthetic leg and fairing may be modified to use lighter weight materials. Ideally, the leg should be as light as possible while providing the required strength for the user.

In a brace embodiment, the brace can be designed by scanning an injured limb and using the surface data to produce a brace having an inner surface that corresponds to the surface data of the injured limb. The brace design process is described in U.S. Pat. No. 7,797,072 which is incorporated by reference. Once the design is finalized, the design data produced by the CAD system can be used to fabricate the prosthetic leg or brace and the fairing. In an embodiment, the prosthetic leg can be fabricated as one or more non load-bearing components that surround an internal load-bearing member that supports the user's weight. Alternatively, the leg can be fabricated as an integrated structure having an outer surface that is part of the load-bearing member. The prosthetic leg can have an exterior shell coupled to an internal framework that can provide additional mechanical strength. The design data can include a series of cross sections that define outer wall and any internal framework along the length of the prosthetic leg which is used to fabricate the prosthetic leg. In other embodiments, the prosthetic leg or brace can be a completely hollow monocoque design that as an exterior shell that provides the required load-bearing strength to support the expected loads.

In the preferred embodiment, the prosthetic leg and brace are fabricated through a rapid prototyping process that uses an energy beam directed at a bath of material. Similar fabrication processes are known as additive manufacturing, rapid manufacturing, layered manufacturing, 3D printing, laser sintering, electron beam melting (EBM) and fused material deposition (FDM). These fabrication processes use an energy beam that is deflected across the material and causes the exposed material to harden.

The cross section design data is used by the fabrication machine to construct each of the leg or brace components in a sequential series of layers. As each layer of material is hardened, the completed portion of the leg or brace component is moved vertically into the bath and the next cross section layer is formed and fused to the adjacent formed layer. When all layers are formed, the prosthetic limb or brace is completed. In an embodiment, the lower leg, upper leg, socket, brace and fairings can be fabricated as separate components that are assembled to create the prosthetic leg. Since the foot and knee may be off the shelf components, these parts may not need to be fabricated.

The fairing fabrication method will depend upon the selected materials and design. If the fairing is made of a thin flexible material such as leather, the fairing design data can be used by a computer controlled cutting machine to precisely cut the fairing material to the design shape. Alternatively, the fairing can be fabricated from a flexible plastic material or sheet metal to form a three dimensional fairing that can match the contours of the outer surface of the prosthetic leg or brace using the rapid prototyping methods described above. The fairing can be placed around the prosthetic limb or brace and the inner surface of the fairing can correspond to a mirror image of the outer surface of the intact limb or an outer surface of the injured limb.

It is also possible to combine different fairing components. For example, a curved plastic fairing can be covered with a thin flexible material such as leather. Thus, the fairing can be made of both plastic and leather.

Additional processing of the leg components, brace and fairing can be performed prior to assembly to obtain the desired appearance. Surface treatments can include metal plating, painting, covering, texturing, etc. For example, if a metal finish is specified, the components can be plated with a layer of metal using known metal layer deposition processes. Additional surface processing can be applied to the metal layer. For example, the metal layer can be brushed, polished, sand blasted, etc.

The prosthetic leg or brace can be assembled once all of the components are formed and the surface finishes are applied. The fairing can be attached to the leg or brace with an adhesive or fasteners. Alternatively, the fairing may be clamped around the prosthetic leg or brace if it is more rigid and the fairing surrounds a portion of the leg or brace. The prosthetic leg or brace may also include surface features that function to hold the fairing in place. For example, a recess that corresponds to the edge of the fairing can be formed in the outer surface of the prosthetic leg or brace.

BRIEF DESCRIPTION OF THE DRAWINGS

The invention will be more fully understood by reference to the following detailed description of the invention in conjunction with the drawings.

DETAILED DESCRIPTION

Figure 1:
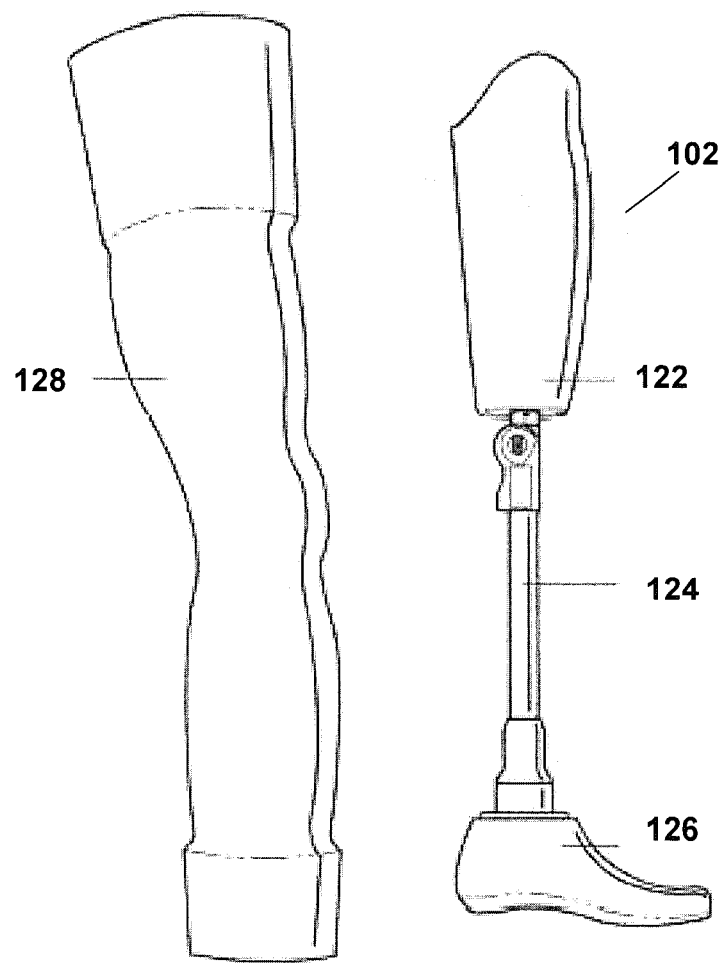
FIG. 1 is a view of a prior art prosthetic leg.

The present invention is a prosthetic limb having an exterior surface that matches the surface contours of a human limb or a brace having an interior surface that matches the surface contours of a human limb. The exterior surface can also be modified so a user can alter the appearance of the prosthetic limb or brace. A replaceable fairing can be designed to cover a portion of the prosthetic limb or brace. The prosthetic limb, or brace and fairing are designed on a computer and the design data can be used to fabricate the prosthetic leg or brace components using computer controlled fabrication machines. The prosthetic limb or brace is preferably designed by a designer using a Computer Aided design (CAD) program.

The inventive prosthetic leg embodiments include a load-bearing component that functions as the human tibia. The upper end of the load-bearing component is attached to a socket that engages the end of the amputated limb and the lower end of the load-bearing component is coupled to an artificial foot. The foot can be flexible and allow for movement between the load-bearing component and the artificial foot. The foot may also include energy storing components that improve the physical performance of the prosthetic leg when the user is running. The mechanical data for the prosthetic leg that may include the relative positions of the socket, knee and foot as well as the movement of these components can be provided by a prosthetist. This mechanical data is input into a CAD program that is used to design the rest of the prosthetic leg. An example of a suitable CAD program is Pro/Engineer by Parametric Technology Corporation. Other CAD software includes: SolidWorks by SolidWorks Corporation a subsidiary of Dassault Systèmes, S. A.

In a preferred embodiment, an exterior surface of the prosthetic leg is a mirror image that is matched to the user's intact leg. Photogrammetry in its broadest sense reverses the photographic process by converting flat 2-dimensional images of objects back into the real 3-dimensional object surface. Two or more different photographs are required to reconstruct a 3-dimensional object. In a perfect photogrammetry process, two photographs would provide enough information to perfectly reconstruct the 3-dimensional object. Unfortunately, the photography and measuring process are generally not perfect so the reconstruction of the 3-dimensional object based upon two photos will also have defects. The photogrammetry object measurement process can be improved by taking more photographs and using the extra information to improve the accuracy. The photogrammetry process will produce a set of 3-dimensional coordinates representing a surface of an object from the measurements obtained from the multiple photographs.

Photogrammetry uses the principle of triangulation, whereby intersecting lines in space are used to compute the location of a point in all three, XYZ dimensions. In an embodiment, multiple cameras are used to photograph the leg or body part simultaneously. In order to triangulate a set of points one must also know the camera positions and aiming angles also called the "orientation" for all the pictures in the set. A process called resection does the camera position and aiming angle calculations for each camera. The cameras should also be calibrated so their errors can be defined and removed.

Triangulation is the principle used by photogrammetry to produce 3-dimensional point measurements. By mathematically intersecting converging lines in space, the precise location of the point can be determined. Photogrammetry can simultaneously measure multiple points with virtually no limit on the number of simultaneously triangulated points. By taking pictures from at least two or more different locations and measuring the same target in each picture a "line of sight" is developed from each camera location to the target. Since the camera locations and aiming directions are known, the lines can be mathematically intersected to produce the XYZ coordinates of each targeted point.

Resection is the procedure used to determine the coordinates of the object from photograph data, based upon the camera positions and aiming directions, also known as the orientation of the camera. Typically, all the points that are seen and known in XYZ coordinates in the image are used to determine this orientation. For an accurate resection, you may have twelve or more well-distributed points in each photograph. If the XYZ coordinates of the points on the object are known, the camera's orientation can be computed. It is important to realize that both the position and aiming direction of the camera are needed for resection. It is not sufficient to know only the camera's position since the camera could be located in the same place but be aimed in any direction. Consequently, the camera's position which is defined by three coordinates, and where it is aimed which is defined by three angular coordinates must be known. Thus, although three values are needed to define the X, Y and Z coordinates of a target point, six values may be required to define a point on a picture, XYZ coordinates for position, and XYZ angles for the aiming direction.

The surface being photographed should also have a minimum number of well-distributed reference points that appear on each photograph and for an accurate surface measurement. The reference points can be visible marks placed on the object that provide a visible contrast that will be clearly shown on the photographs. There should be at least twelve well-distributed reference points on each photograph and at least twenty points for the entire surface of the object. The reference points should be evenly distributed on the object and throughout the photograph. The surface of the object can be more accurately measured with a larger number of reference points.

Figure 2:
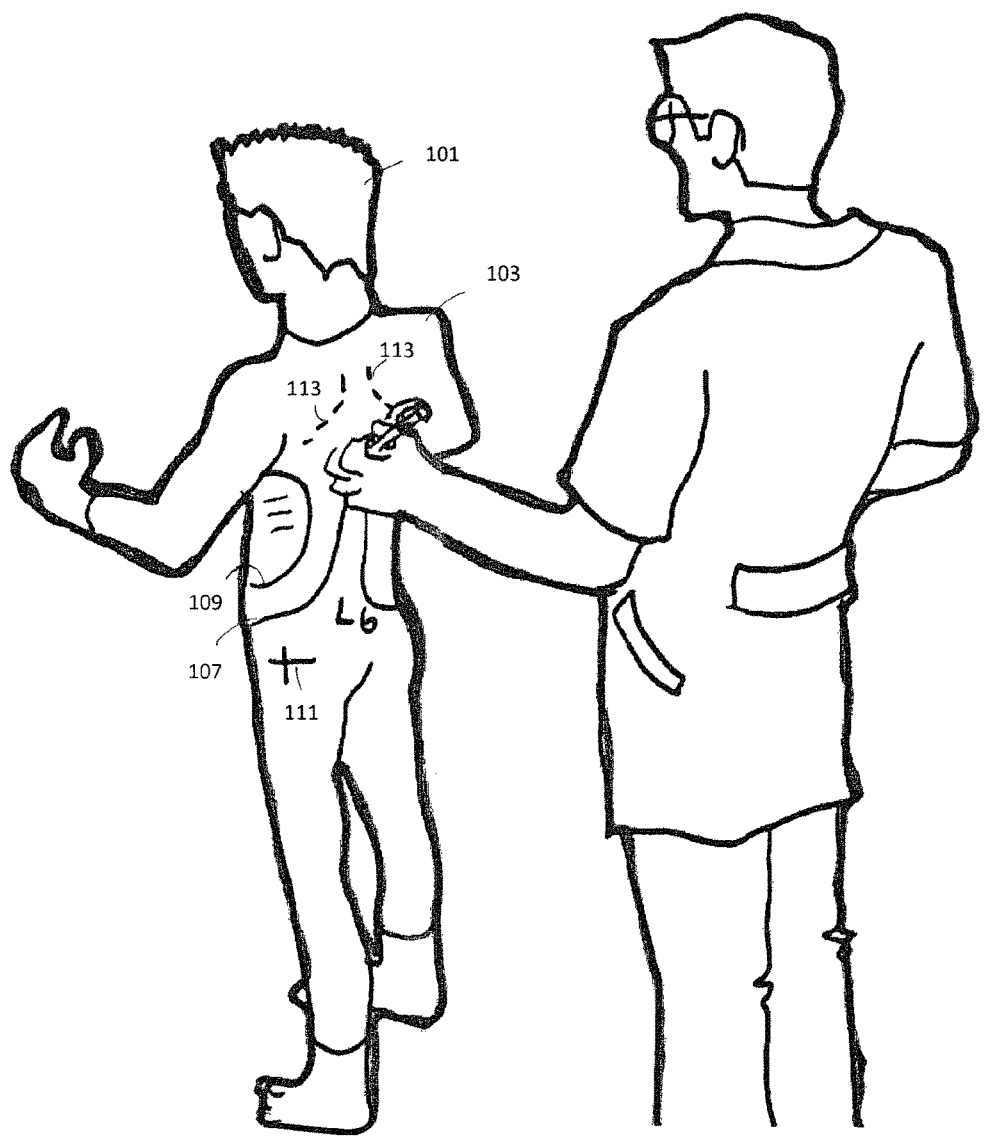
FIG. 2 illustrates a patient being marked by a doctor for back brace fabrication.

While it is possible to mark the patient's skin with markings, in a preferred embodiment, the patient is covered with a form fitting material such as an elastic cotton tube, stockinette, leotard, body suit. In other embodiments, the body can be wrapped with a form fitting material. In another embodiment, the body surface can be sprayed or painted with removable materials such as a flexible plastic or rubber material that conforms to the body and can marked and easily removed after images are captured. With reference to FIG. 2, a patient 101 is illustrated wearing a body suit 103 that covers the patient's body, arms and legs. Thus, the markings can be applied to the form fitting material rather that the patient. The markings can include: ink, pencil, crayon, grease, graphite, tape or any other particles released by a marking device. In other embodiments, the markings can include chemical or magnetic reactions between a pen tip and the material covering the patient or other markings. The pen tip can be moved over the material to create chemical reaction or magnetic material lines that are visible. The markings can also include: adhesive stickers, light points or a light grid projected onto the patient.

In an embodiment, a computer program processes the photographic measurements to produce the final XYZ coordinates of all the measured points. In order to do this, the program triangulates the target points and resects the pictures. The program may also calibrate the camera. Typical accuracies of the three dimensional measurements can be very high under ideal operating conditions. For example, the measurements can be accurate to 50-100 microns (0.002" to 0.004"). However, the accuracy of a photogrammetric measurement can vary significantly since accuracy depends on several inter-related factors. Important accuracy factors include: the resolution and quality of the camera, the size of the object being measured, the number of photographs taken, and the geometric layout of the pictures relative to the object and to each other.

Photogrammetric measurements can be dimensionless. To scale a photogrammetric measurement, at least one known distance is required. The known distance can be a distance marked on the object. For example, if the actual coordinates for some targeted points are known, the distances between these points can be determined and the points can be used to scale the measurement. Another possibility is to use a fixture with targets on it and measure the fixture along with the object. Because the distance between the targets on the fixture is known, it can be used to scale the other measurements between reference points on the object. Such fixtures are commonly called scale bars.

In an embodiment, the inventive method is used to make a cast or a brace for an injured limb. A series of photos are taken of the injured limb. If the bone is broken, fracture should be reduced before the photos are taken. The photogrammetric processing methods described above are then used to obtain the surface coordinates of the injured limb. In order to define common surface points on the limb, reference points can be placed on the limb. The reference points can simply be any contrasting color or reflective points, patterns, shapes, objects, symbols or other optical indicators which are easily visible. In the preferred embodiment, the reference points are placed and evenly distributed around the entire limb or portion of the body that the brace is being constructed for.

In addition to the reference points, the patient can also be marked to define an edge of the brace or other features. With reference to FIG. 2, the doctor can mark the body suit 103 with a pen 105 to define the locations of the edge of the brace. The edge marking can be one or more continuous lines 107 that extend around the body or limb. In other embodiments, the edge can be defined by a series of marks that define the edge of the brace and are connected during the brace design. Additional lines 109 can also be marked on the patient to create openings in the brace. For example, the patient may have injured areas from an operation that has been closed with stitches and should not be in contact with the rigid brace. By providing an opening in the brace, the patient's stitches will not be pressed against the brace structure. In FIG. 2, the doctor has drawn a circle around this portion of the patient's body so that the brace can be designed with a cut out for this area. The doctor can also make notes on the body suit 103. The doctor has written "L6" in ink on the patient to indicate the location of the L6 disk. The doctor has also marked a cross 111 in ink at the greater trochanter of the femur and dashed lines at the shoulder blades 113. These anatomical locations are important in the design of the brace and are therefore marked on the body suit 103. The marking used to define the lines, brace edges, holes and annotations can be black or colored ink, pencil, crayon, grease, graphite, tape or any other visible line markings. Because photogrammetry uses photographs, the digital pictures will record all of the lines or other markings.

Figure 3:
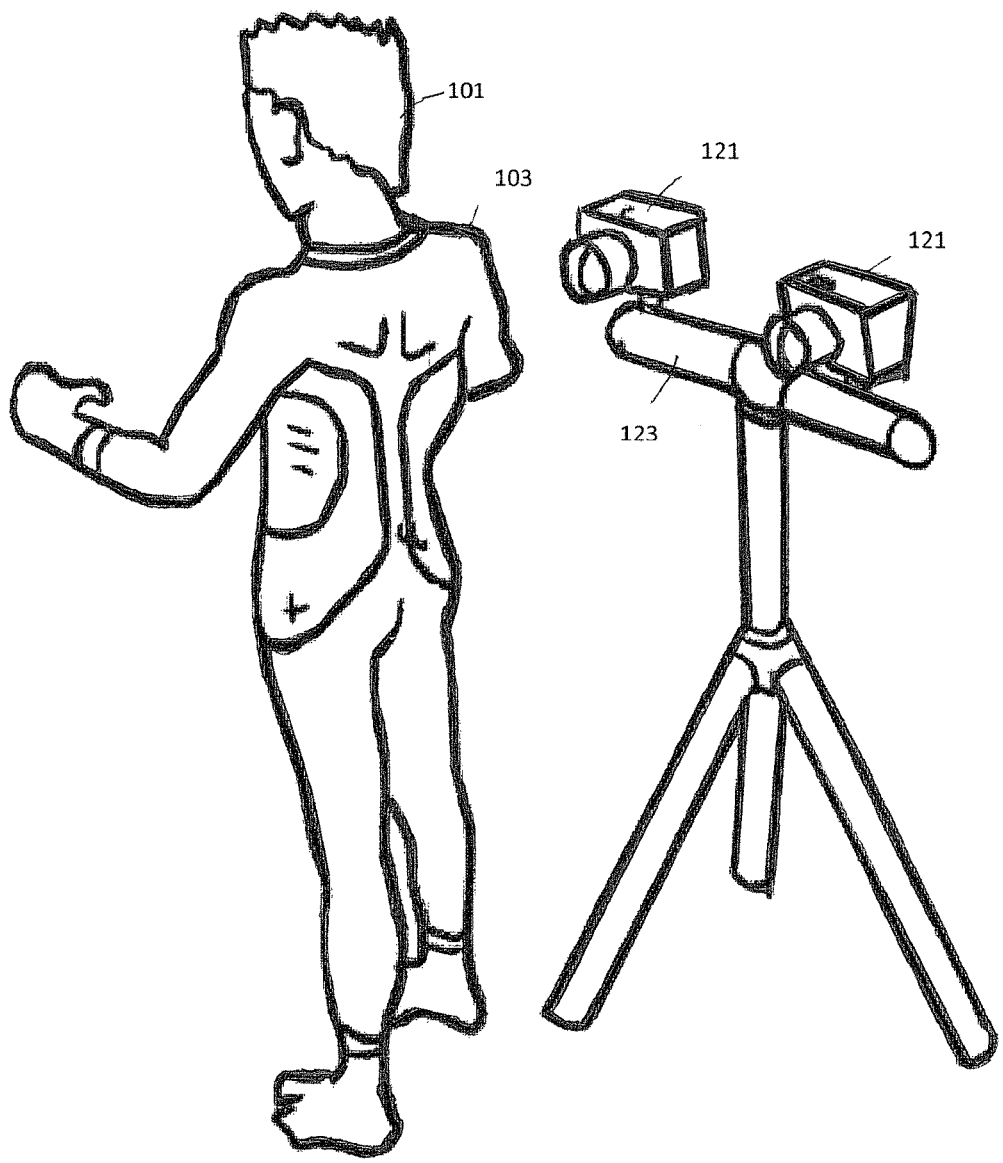
FIG. 3 illustrates the marked patient being photographed.

With reference to FIG. 3, photographs of the patient are taken with a plurality of digital cameras 121. In this example, the cameras 121 are mounted on a bracket 123 and horizontally separated by a known distance. The cameras 121 have the same horizontal position and the lens can be in the same plane and angled inward towards each other. The angle of the lenses can be between about 5 to 45 degrees. The distances between the patient 101 and the cameras 121 are also known. The two cameras 121 can be actuated simultaneously so that the two or more photographs will represent the patient 101 in the same position. In order to get the body contour information, pictures are taken of the patient 101 wearing the marked body suit 103 from various angles around the entire circumference so that all surfaces of the body will be covered by the brace. Each photograph should include at least twelve of the reference points. By processing the photographs and triangulating the reference points and other lines and markings in the photographs, the coordinates representing the body surface can be obtained.

Figure 4:
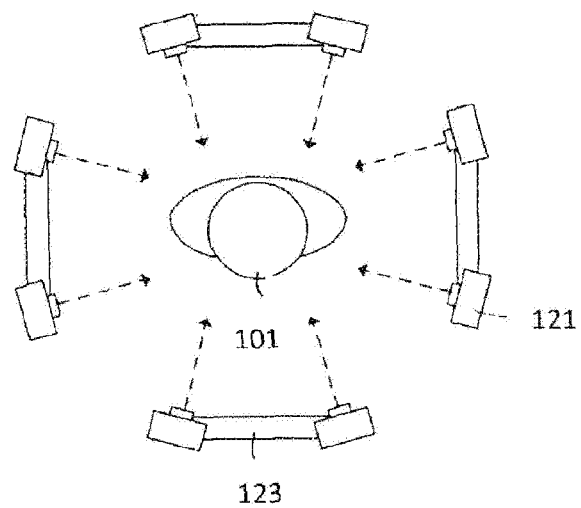
FIG. 4 illustrates a top view of a patient being photographed by a plurality of cameras.

With reference to FIG. 4, a top view of a camera 121 system used to photograph the patient 101 and body suit 103 is illustrated. In an embodiment, an apparatus that includes a plurality of cameras 121 that are mounted on brackets 123 and positioned around an open space can be used to photography the patient 101. The cameras 121 are pointed in towards the patient 101 and arranged in groups of two cameras 121. The cameras 121 can be mounted on brackets 123 that hold the cameras so they are generally pointing in the same direction but angled slightly towards each other. The cameras 121 can be positioned with the lenses horizontally aligned, but rotated slightly about a vertical axis, so the camera 121 lenses are not parallel. This angle allows the cameras 121 to analyze the difference in the surfaces so that a 3-dimensional representation is generated, much as it is with human stereoscopic vision.

In this example, four groups of cameras 121 are mounted around the patient 101 with each group having two cameras 121. Thus, eight photos each from different angles are taken of the patient 101. The pictures taken by the cameras 121 together cover the entirety of the torso. The camera 121 positions can be moved depending upon the area of interest. In the illustration, the cameras 121 may be configured to collect data for a back brace. However, if a leg brace is being made, the cameras 121 can be lowered to a position around the leg.

An actuator can be coupled to each of the cameras 121 and used to cause all of the cameras to photograph the limb simultaneously. Alternatively, the camera 121 pairs can be synchronized to all take pictures simultaneously to capture the images of the object at the same time. Since the shutter speed is typically just a fraction of a second, there is no need to keep the patient 101 absolutely still for an extended period of time. In other embodiments, a single camera can be used to capture multiple images of the patient. In this embodiment, the camera can capture multiple images simultaneously or in a short period of time. The camera can have multiple lenses each capturing a different image. Alternatively, the patient can move relative to the camera. By rotating the patient or rotating the camera about the patient and taking multiple photographs, a single camera can capture multiple images that can be used to obtain the surface topography and other marker data.

As discussed above, the photographs are processed and used to generate three dimensional data that accurately describes the outer surface of the patient 101. The three dimensional data is then used to design and fabricate the brace or cast. Because the surface data is very accurate, the brace or cast will have a custom fit that accounts for all detected surface contours. In addition to the custom fit interior surface, the edges or brace features are also clearly defined by the edge or feature markings and can be used to assist in the design of the brace or cast.

In some cases, the physical condition of the patient is such that the photogrammetry images will not result in an accurate brace. For example, if a patient has injured a limb, the area of injury can be swollen. Thus, any photographs of the limb will result in a scan data that is much larger than the unswollen limb. In an embodiment if the patient has an intact limb that is similar to the damaged limb, the intact limb can be photographed and the surface data obtained from the intact limb can be reversed in a mirror manner to create the required data for a brace for the damaged limb. The brace can be designed and fabricated so that when the swelling goes down, the brace will be ready for the patient.

Photogrammetry also has various benefits over other types of surface scanning methods including optical and laser scanning because it can also be used to detect markings placed on the patient by a doctor which can be used to indicate special portions of a body or the brace. For example, a doctor can draw on the patient to demark any number of notes in ink or other markings on the patient that they will reference later in the custom device process. These marking may indicate: boundaries of the custom prosthetic/orthotic, areas of bony protuberances, folds of adipose tissue, specific reference vertebrae, sensitive areas on the body (rashes, birthmarks, moles, etc.) to be avoided, areas that will require enhanced ventilation, clearance areas around joints to allow unencumbered motion, setup notes, reference boundaries for 'shims' which will later add additional pressure within the brace and various other information. The body markings can be colored points, lines or symbols, textured markers, reflective or other codes that are used to identify the different types of reference points on the patient. For example, a patient may be marked with a first color to indicate a desired boundary of the brace or cast. The patient can also be marked with a second color or textured marker to indicate a bony protuberance or sensitive areas. Since the bony protuberances, or underlying bony anatomy are areas prone to skin breakdown, the brace can have special features over these areas to avoid abrasion or damage to these areas. For example, during the design process, the operator can reduce the brace over the areas of the patient's body marked as bony anatomy. An example is the placement of the brace over the regions of the scapula. The scapula and its borders can be palpated manually but are difficult to determine based on surface morphology. The brace must accommodate for the scapula to function properly. In the techniques the location of the edges or body of the scapula is marked on the patient and the body of the brace will accommodate the bony edges with custom padding or relief in the brace contour.

The brace will require pads to be comfortable to the patient. The locations of the pads can be marked on the patient as described above. For example, a pad location and shape can be indicated with a coded marking in the shape of the pad. The CAD system will detect the pad marking and be able to fabricate a pad that matches the designated shape. During the fabrication process, the pads can be fabricated from a soft elastic material in a range of thicknesses and firmnesses. For example, the CAD data can be used to cut the pads from a sheet stock of pad material. The CAD system can also design the brace to accommodate the pads. For example, the brace can be designed and fabricated with recesses formed at the coded and marked areas or other attachment mechanisms. Since the patient surface data is used to form both the brace and the pads, they will fit together very accurately. If there are ventilation holes designed into the brace over a pad location, the pad can also be designed with ventilation holes that is aligned with the ventilation hole in the brace.

When the brace is fitted to the patient, the doctor will have a plurality of pads and will be able to select the best pad thickness for the patient. Because the brace can be made of a strong and durable material, the pads can be worn with use of the brace and may need to be replaced periodically. The doctor can have additional pads fabricated from the brace data. Additional pads can also be made using additive manufacturing processes such that the pads have an outer surface that is conforming to the brace and an inner surface that is conforming to the patient's anatomy in areas with complex surface geometry such as bony prominences such as the iliac crest.

In other embodiments, the coded marking can be a pattern, symbol, a textured pad, bar code, 3-D objects or other indicators placed or marked on the patient. The coded markings can be black or colored ink, pencil, crayon, grease, graphite, tape or any other visible line markings. Because these cameras use the photographic image for their data input, the coded markings or topography on the patient can be identified by the brace/cast design software. The inventive process may be able to distinguish different color codings as well as different pad textures. The textures can include grooves, etched patterns, convex or concave surfaces, etc. Each texture may represent a different feature of the brace at the marker location. The detection system software may automatically detect and identify the coded color or texture. The software can then automatically design the requested feature of the brace associated with the coded color or texture was positioned on the patient. The additional markings will be transferred to the digital representation of the patient and be used to help design the brace or cast.

Figure 5:
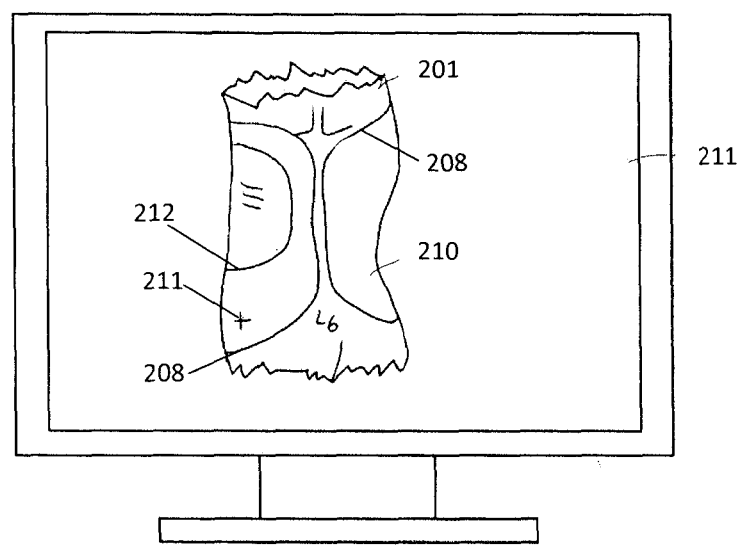
FIG. 5 illustrates a computer displaying a digital representation of a portion of the patient.

The process by which the scanned body data is used to design a brace is illustrated in FIGS. 5-9. FIG. 5 illustrates a scanned image of a human torso 201 on a CAD screen 221. The contours of the torso 201 are accurately measured and the additional markings that were placed on the patient are also illustrated on the scan data. In this example, the doctor has drawn a cross 211 of the patient's greater trochanter of the femur so the brace is designed with extra space in this area for movement of the leg. Line markings 208 indicate the desired boundaries of the brace and line 212 indicates a hole in a side of the brace. The notation "L6" written in black or colored ink, pencil, crayon, grease, graphite, tape or any other visible markings media is also visible or detectable from the photogrammetry scan data.

Figure 6:
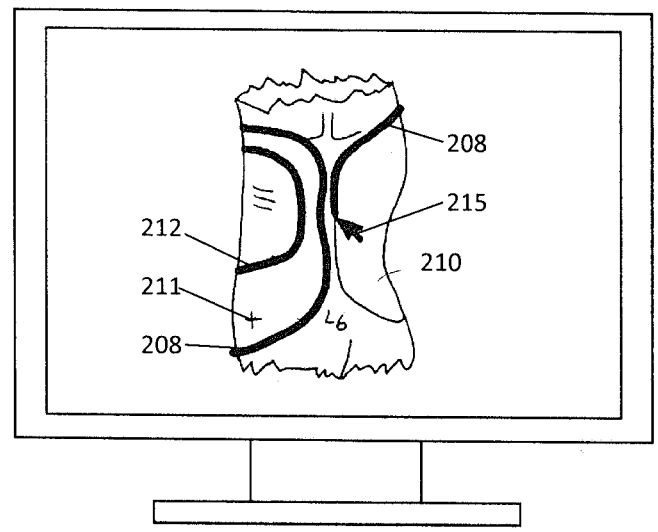
FIG. 6 illustrates a computer displaying the design process for a back brace.

With reference to FIG. 6, the line 208 representing the edge of the brace is being highlighted. The line 212 representing a hole to be formed in the brace has been highlighted by the brace designer. In this embodiment, a mouse controlled cursor 215 is used to highlight the lines. In other embodiments, the designer can select click on the line to highlight the entire line. In this example, the darker line represents the portions of the line to be removed from the brace. However, any other visual markings can be used to identify the portions of the line to be removed.

In some situations, the brace or device may not perfectly match the scanned surface data of the patient. For example, the designer can also account for the marked cross 211 representing the location of the greater trochanter of the femur bone. The marking will be indicated on the images captured during photogrammetry and the cross may be a designated symbol indicating the location of the greater trochanter. The software can then adjust the design of the brace over the greater trochanter by expanding this portion of the brace.

In another example, a patient may have scoliosis and may need a corrective back brace that changes the normal posture of the patient. The brace may be used to correct the curvature of the back to reduce the curvature deformity. Photographs of the back can be taken to obtain the surface data as described above. However, the actual spine position may not be detected unless the surface shows the back bones as surface features. In order to clearly indicate the spinous processes of the back, the doctor may need to mark the location of each. The marking can be coded to indentify the specific bones or indicate a bone that is damaged. The marks can be black or colored ink, pencil, crayon, grease, graphite, tape or any other visible line markings. The markings can surround the bones, be a cross mark, or any other mark that clearly identifies the locations of the bones. When the photogrammetry images are processed, the locations of the spinous processes will be clearly indicated. The back surface and spinous processes locations can then be used to design the back brace.

Rather than designing a back brace that uses the detected spine position, the back data can be modified to create a brace that straightens the patient's back. The designer can obtain measurements for the overall length and curvature of the spine and the desired curvature alteration of the brace. The difference between the brace and the normal back position can be specified by the patient's doctor. The designer can then adjust the recorded back curvature to design a back brace that is straighter while maintaining the desired interior volume defined by the brace. In an embodiment, the design program can include a system for adjusting the brace design which allows for the adjustments of one part of the brace to be carried over to the other portions of the brace. For example, if the back data shows the photographed spinal curvature, the designer can manipulate the apex to reduce the curvature. Rather than adjusting only the apex portion, the program will make similar adjustments to the surrounding portions of the brace so that the corrective brace will properly fit the patient. For example, the brace can be divided into many different thin horizontal sections that may each correspond to a different spinous process. When one section is moved, the other sections will move to a lesser degree so that the scoliotic curvature is reduced. An algorithm may be used to scale the movement of the other sections of the brace on the CAD design. By automatically adjusting the different sections of the brace when one section is moved, the brace design is simplified and accurate.

In other embodiments, the designed brace or cast can vary from the photogrammetry measurements taken of the patient. For example, the patient may be swollen due to trauma or inflammation. The brace design system can account for the swelling and allow the designer to create a smaller brace that will fit the patient after the swelling is reduced. In an embodiment, the system can use photographs of an intact limb and use the mirror image surface data as a guide for the brace for the swollen limb. The intact limb may not be a perfect match of the damaged limb, but in many cases it is sufficiently accurate to form a suitable brace or cast.

Figure 7:
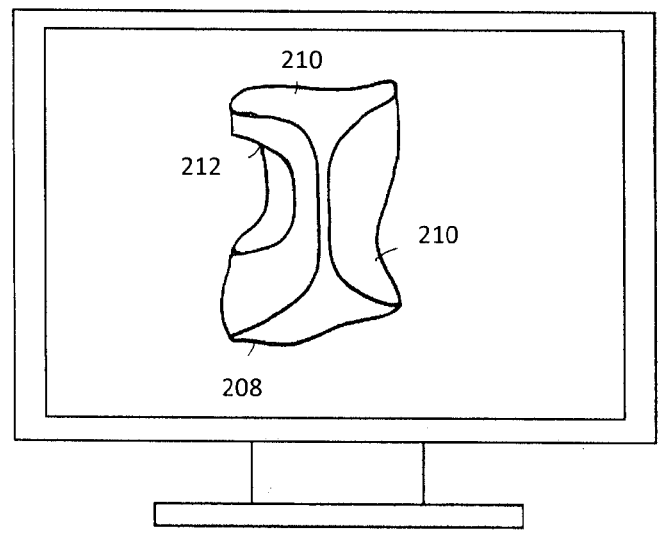
FIG. 7 illustrates a basic back brace designed from the digital representation.

In FIG. 7, the torso is illustrated with the area inside the hole line 212 and torso areas outside the edges 208 removed. Although not shown, designer operating the CAD software can rotate the illustrated torso to show any view of the brace 210. A material thickness can be added to the interior torso surface to create the basic brace design. Because the markings are accurately detected by the photogrammetry system, all of the marked edge and hole positions are transferred to the digital representation and the required brace boundaries and features are accurately identified without having the re-examine or re-measure the patient. The process completes the basic design of the brace 210.

Figure 8:
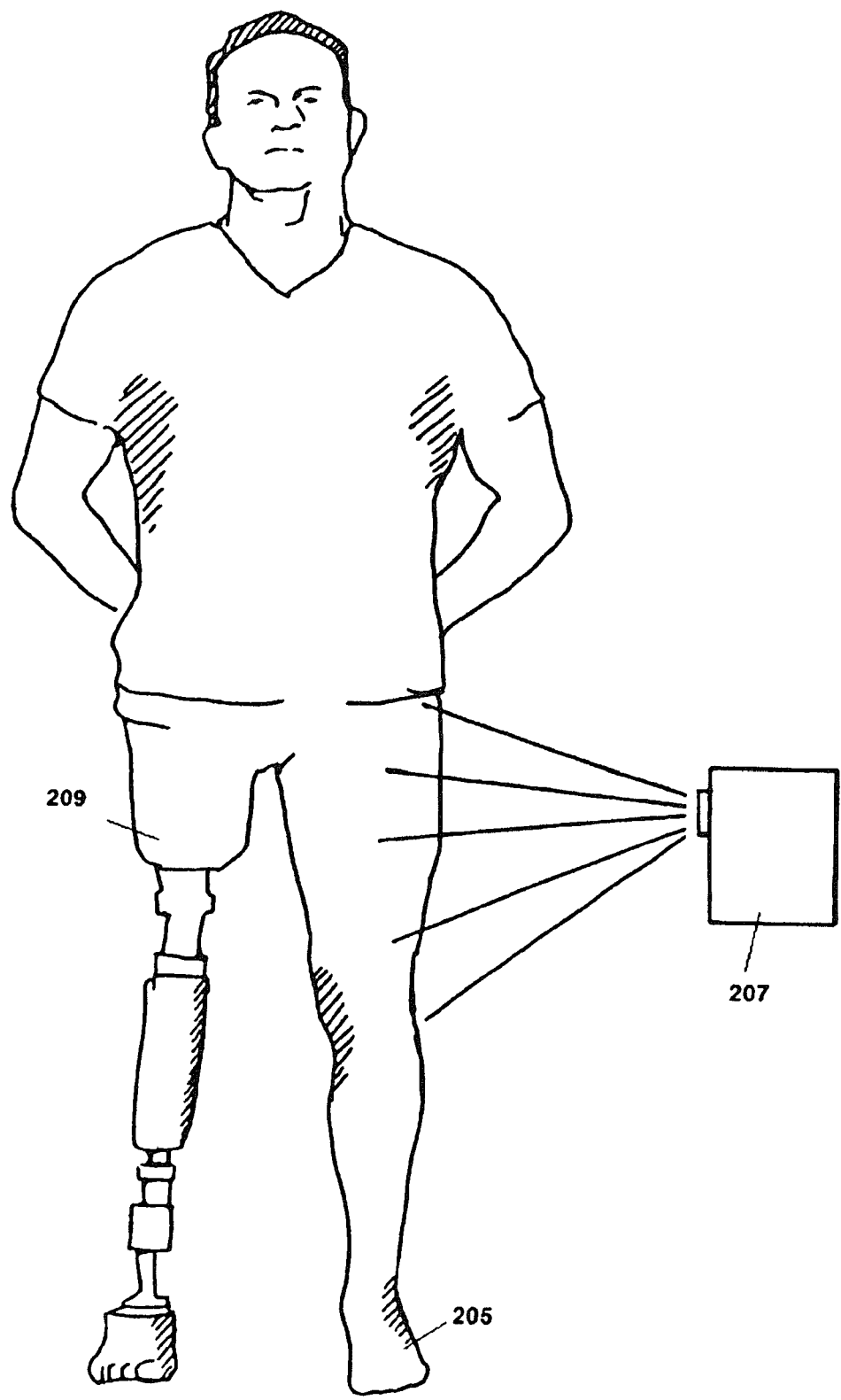
FIG. 8 is a view of a scanning device used to measure an intact leg and an end of an amputated limb.

A similar photogrammetry process can be used to create an external surface shape of a prosethetic limb. In other embodiments, the surface data of the intact leg can be obtained through a photogrammetry process and input into the CAD program. With reference to FIG. 8, the intact leg 205 is photographed by digital cameras 207 from multiple sides to obtain a full three dimensional digital image. The digital cameras 207 create a data set of geometric measurements for many points on the surface of the leg 205. The accuracy and detail of the three dimensional digital image is improved by taking more photographs of the leg 205. In addition to obtaining data for the intact leg 205, the described photogrammetry process can also be used to obtain the surface measurement data for the end of the amputated limb 209. The digital cameras 207 may also be used to collect color information so that the exact color(s) of the intact leg 205 can be determined and used to create the prosthetic leg. While photogrammetry is the preferred method for determining the surface of the intact leg, in other embodiments any other optical, electomagnetic, laser scanning or mechanical method can be used to obtain this information. While some scanning systems are capable of detecting a surface contour with a resolution less than a millimeter, the described scan does not require this level of accuracy to recreate the appearance of the intact leg.

The scan data is converted into a usable surface file that can be read by the CAD program. More specifically, the surface data from a scan of the intact leg 205 can extrapolate the shape of the intact leg 205 through a reconstruction process. The reconstruction process uses an algorithm that connects the adjacent points, known as a point cloud, with lines from the scanned leg data to construct a continuous surface from many small polygon shapes that form a polygon model. The data produced by the reconstruction process is a continuous three dimensional digital representation that closely matches the surface of the intact leg 205. The same reconstruction process can be used to obtain the surface data for the end of the amputated limb 209. An example of the software used to perform the scanner data reconstruction process is Geomagic Studio by GeoMagic and Pro Scan Tools which is a plug in module for Pro/Engineer by Parametric Technology Corporation.

The reconstruction surface file for the intact leg is input into the CAD program. The prosthetic designer can use the CAD program to reverse and manipulate the intact leg data to create a mirror image digital representation. This mirror image data can then be used in the design of the exterior surface of the prosthetic leg. The data representing the surface of the end of the amputated limb 209 can also be manipulated and reversed to create a digital data representing of the interior surface of the prosthetic leg socket. It may be necessary to expand this surface to allow for some space possibly for padding between the socket and the end of the amputated limb 209.

Figure 9:
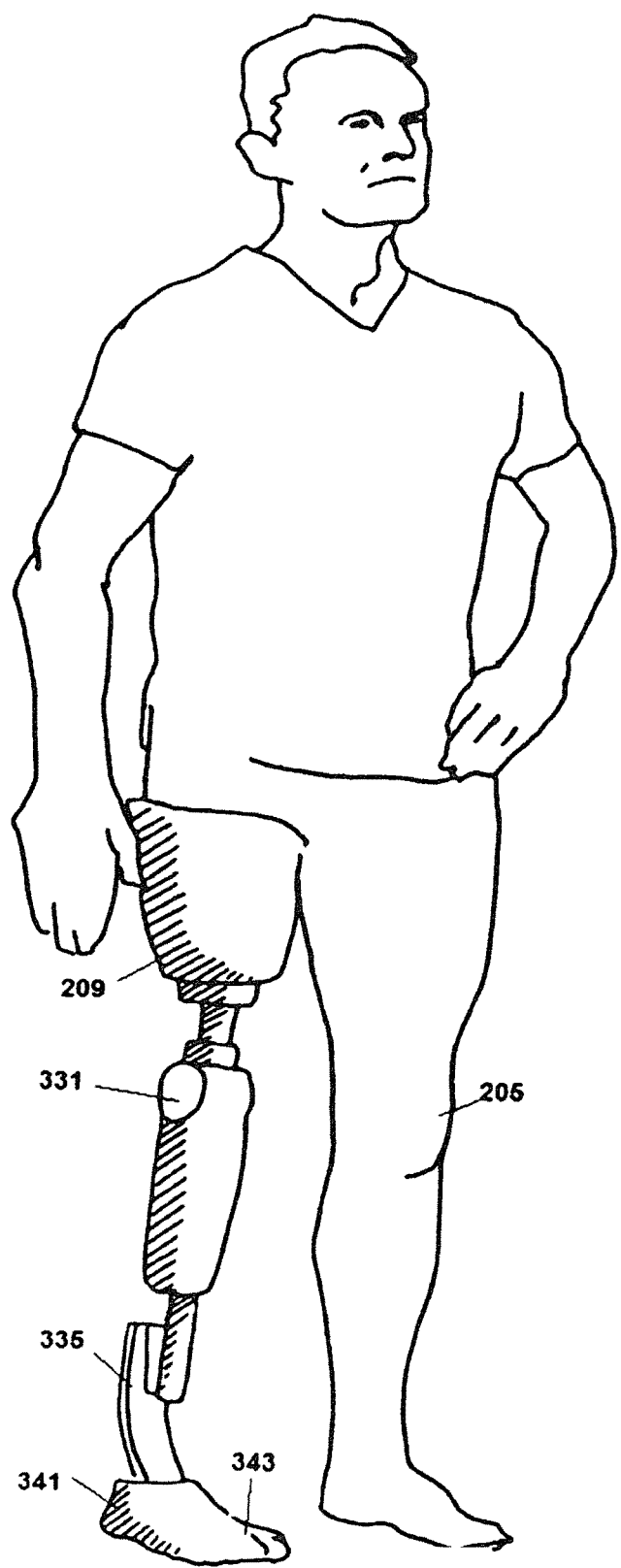
FIG. 9 is a view of load-bearing components of a prosthetic leg.

While the leg and socket data are used to form the outer surfaces of the prosthetic leg, mechanical components are also required for a fully functional design. With reference to FIG. 9, the user can consult with a prosthetist to determine the exact relative placement of the artificial knee 331 and foot 335 in relation to the end of the amputated limb 209. The prosthetist can use the measurement of the intact leg 205 and use this information as a starting point to determine the relative positions of the socket, artificial knee 331 and foot 335 in the prosthetic leg.

The knee 331 can be a stock item that includes a multiple linkage assembly that mimics the movement of a human knee. Different knees may be required for different sized patients and different types of expected use. The dimensions and movements of these knees can be stored in a computer data store. The prosthetist may select the most appropriate knee for the patient and a digital representation of the selected knee 331 may be used to accurately design the prosthetic leg.

The artificial foot 335 used with the prosthetic leg can also be a stock item. Like the artificial knees, digital representations of the various different types of feet may be available. The proper foot may also be selected for the patient by the prosthetist and the digital representation can be used in the design of the prosthetic leg. For example, the foot 335 shown in FIG. 9 is made of a flexible material to provide energy storage and cushioning when compression forces are applied to the heel 341 and toe 343. This type of foot may be particularly useful for a highly active person who would like to run regularly. Alternatively, the foot or a fairing that is placed over the foot 335 can be based upon a mirror representation of the user's intact foot that is created by laser scanning the intact foot as described above.

The placement of the artificial knee 331 and foot 335 relative to the end of the amputated limb 209 are specified by the prosthetist and input into the CAD program. These components can be displayed within the prosthetic leg on a computer. The CAD program can manipulate the components to enlarge, rotate, add or remove or change components and show the movement of the prosthetic leg. All internal mechanical design information can be saved in computer readable format for future modification or prosthetic fabrication.

The internal mechanical component data and mirror image surface data can be joined together in a virtual prosthetic leg created by the prosthetic designer with the CAD program. The joining of the surface data and the internal mechanical components can be done in different ways. In an embodiment, the outer surface is a non load-bearing structure fairing that is made of a thin material and has the mirror image shape of the intact leg. The fairing is coupled to a series of cross section templates and longitudinal members that form an internal framework that are attached to the internal mechanical components. The outer surface is not load-bearing, so the internal components and outer fairing are distinct structures. In another embodiment, the outer surface and mechanical components are designed to be an integrated structure with the outer surface providing part of the load bearing strength.

Figure 10:
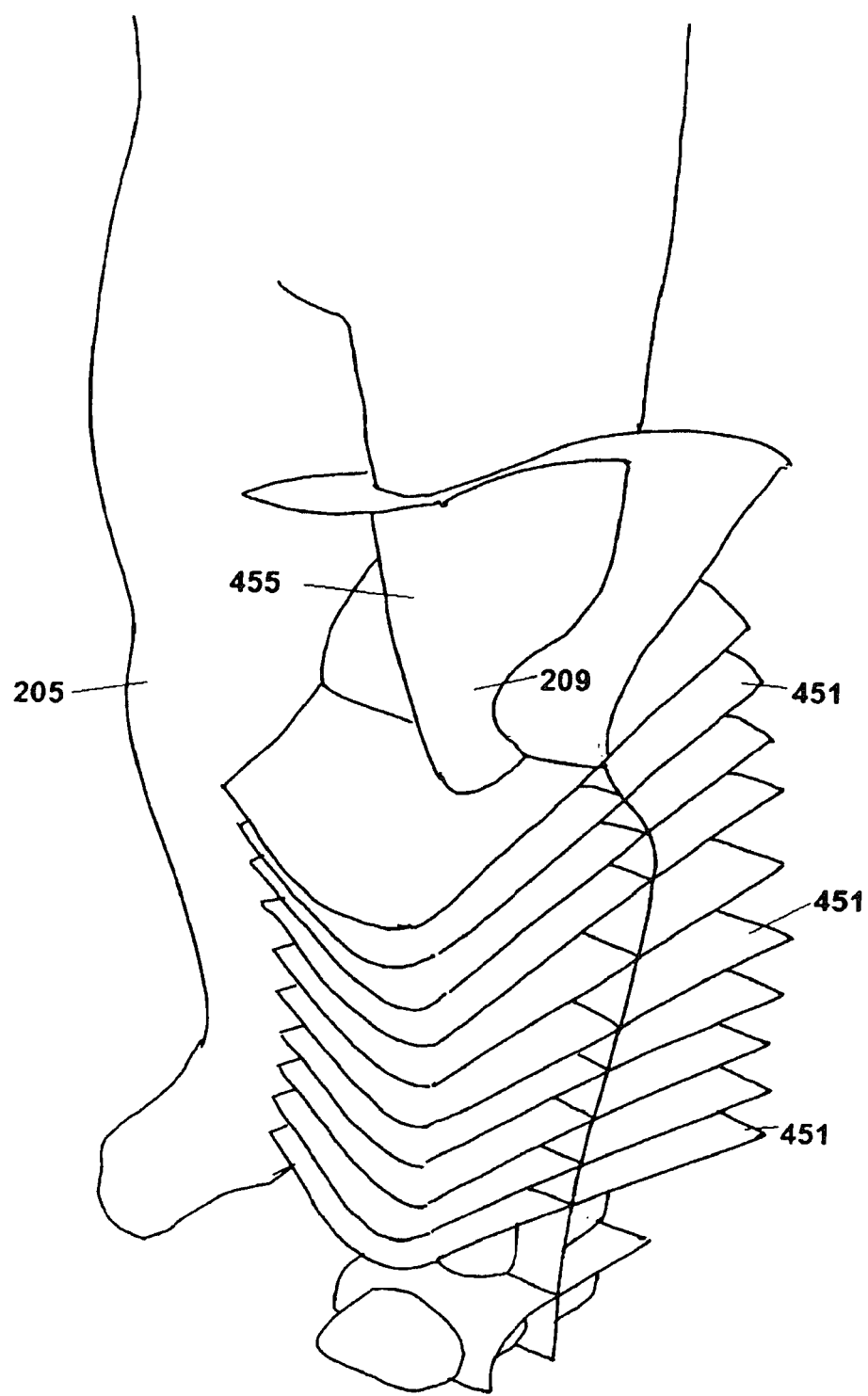
FIG. 10 is a view of load-bearing components surrounded by templates used to design the prosthetic leg.

With reference to FIG. 10, the non load-bearing outer surface embodiment of the prosthetic leg is illustrated. Templates 451 are placed around the internal components in a parallel configuration along the length of the leg. Each template 451 extends beyond the exterior surface and each is trimmed to the corresponding inner surface of the fairing 453. The fairing 453 is placed around the prosthetic leg (or brace) and intersects each of the templates 451. Because the fairing 453 and templates 451 are illustrated in a virtual space, they can pass through each other during the design phase. The fairing 453 can be substantially similar in both the brace and the prosthetic limb embodiments.

Figure 11:
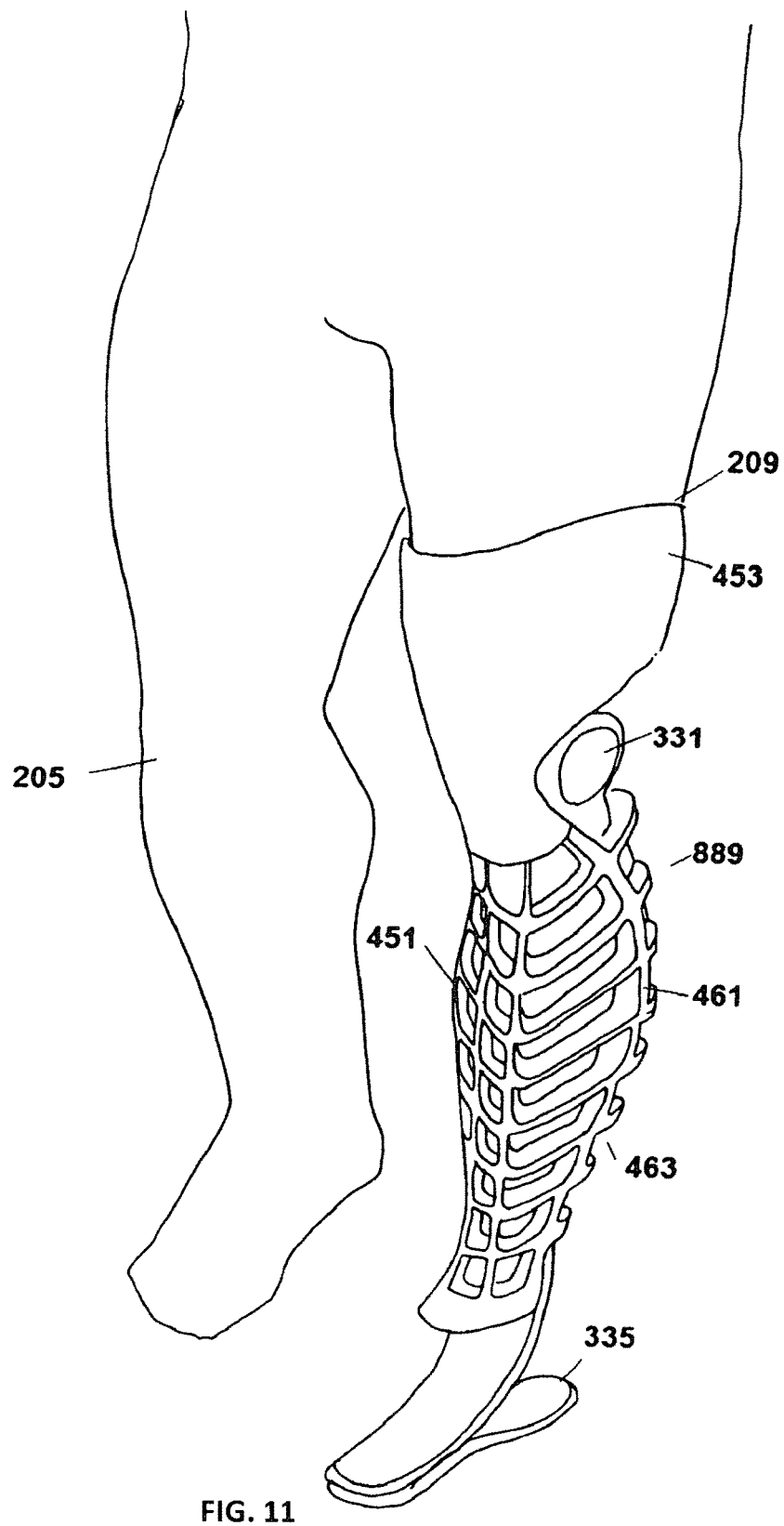
FIG. 11 is a view of the framework surrounding the load-bearing components trimmed to the desired shape.

With reference to FIG. 11, the outer surface of the fairing 453 of the prosthetic leg 889 is shown with the failing 453 removed below the knee 331. The templates 451 are cut to remove the portions of the templates 451 that extend beyond the inner surface of the fairing 453. Additional longitudinal members 461 are attached to the templates 451 and extend along the length of the prosthetic leg 889. The outer edges of the longitudinal members 461 can also correspond to the inner surface of the fairing. The templates 451 and longitudinal members 461 provide an internal framework 463 that helps to maintain the shape of the fairing 453. The prosthetic designer can alter the templates 451 and longitudinal members 461 to control the strength of the framework 463. More templates 451 and longitudinal members 461 of a given strength will result in a stronger framework 463 and prosthetic leg.

In the brace embodiment, the brace can also have templates 451 and longitudinal members 461 that are attached to the templates 451. The interior surfaces of the brace can conform to the exterior shape of the injured limb.

Figure 12:
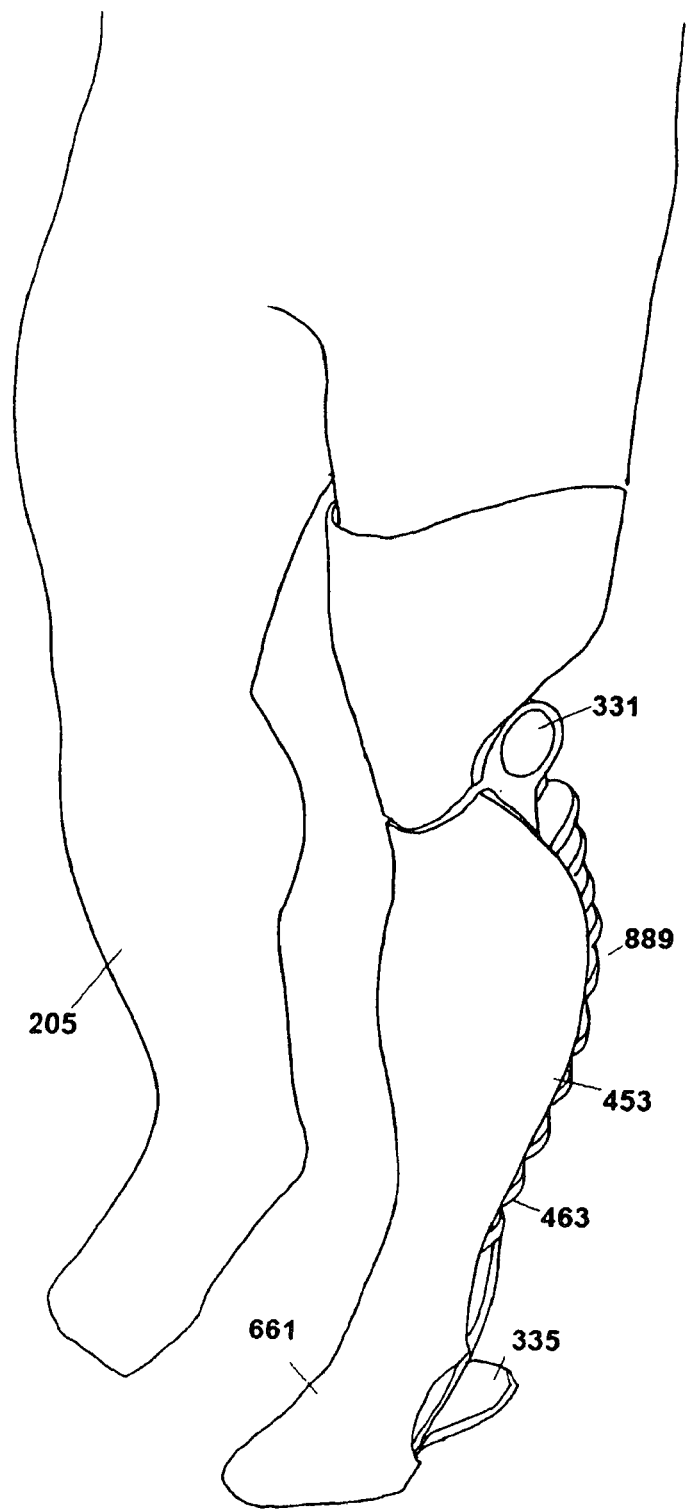
FIG. 12 is a view of a fairing placed over the framework of the prosthetic leg.

The prosthetic designer can also design the fairing 453 to be flexible in areas of the prosthetic leg that move. With reference to FIG. 12, the shin fairing 453 is placed over the frame 463 and foot 335 of the prosthetic leg 889. The non load-bearing fairing 453 may be made of a high strength flexible polyamide such as Nylon 6 or 12. In this embodiment, the fairing 453 wraps around the shin and calf of the prosthetic leg. The fairing 453 also bends with any expected movement of the foot 335 and knee 331. As illustrated, the fairing 453 can be designed to have a narrow section that only covers the front of the knee 331. This thinner fairing width at the knee 331 allows the fairing 453 to be more flexible at this area. The fairing 453 may also be designed to only cover the front of the foot 335 which allows for easier movement. For a close fit, the inner surface of the fairing 453 may match the outer surface of the prosthetic leg 889 framework 463. Thus, the inner surface of the fairing 453 can correspond to the outer surface contours of the patient's intact limb.

Figure 13:
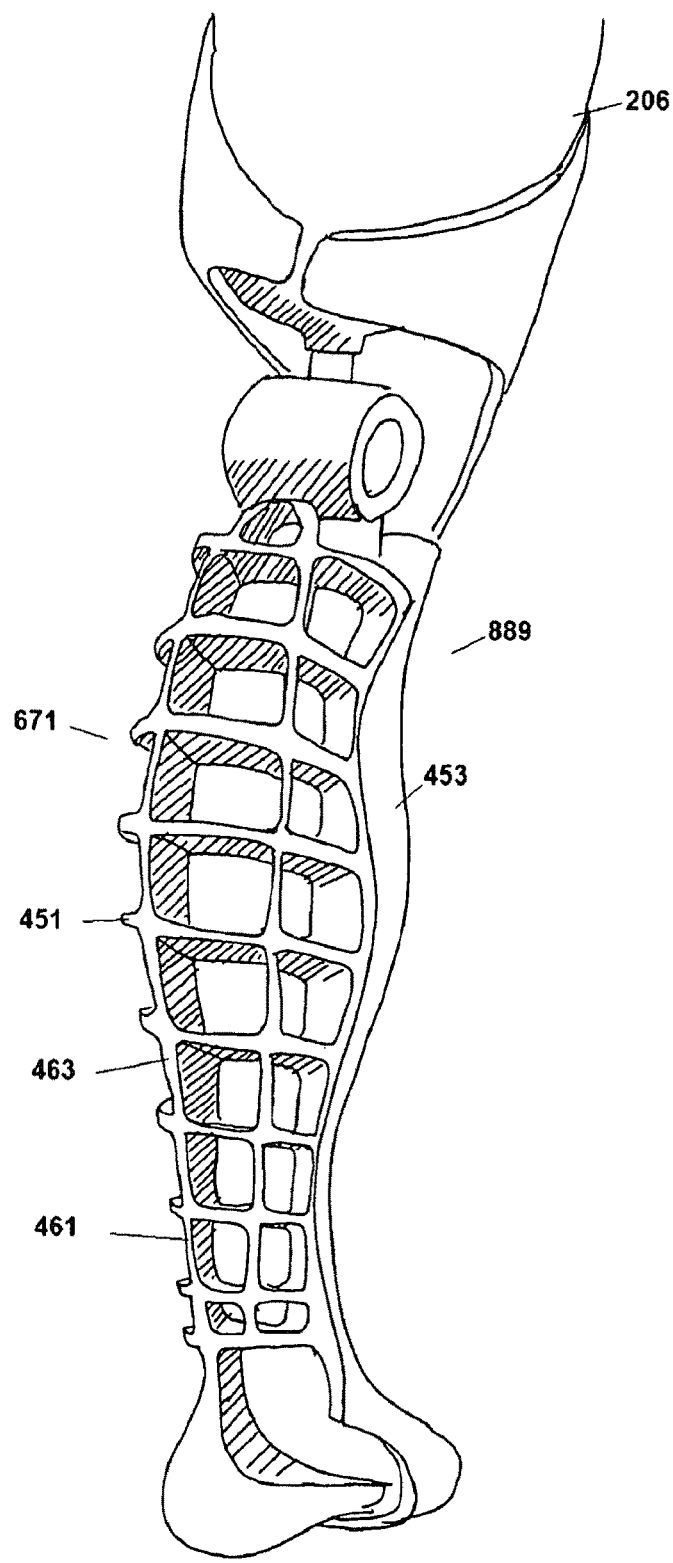
FIG. 13 is a rear view of a shin fairing.

With reference to FIG. 13, the rear portion of the prosthetic leg 889 is illustrated. In this embodiment, the fairing 453 wraps almost fully around the upper portion of the prosthetic leg 889 covering the end of the amputated limb 206 and socket. The fairing 453 does not cover the calf portion 671 and the template 451 and longitudinal members 461 that form the framework 463 are exposed. Like the templates 451, the longitudinal members 461 may extend from the inner load-bearing member to the inner surface of the fairing. In other embodiments, the prosthetic designer can extend the fairing 453 around the calf portion 671 or add a separate fairing that wraps around the calf portion 671 of the prosthetic leg 889.

Figure 14:
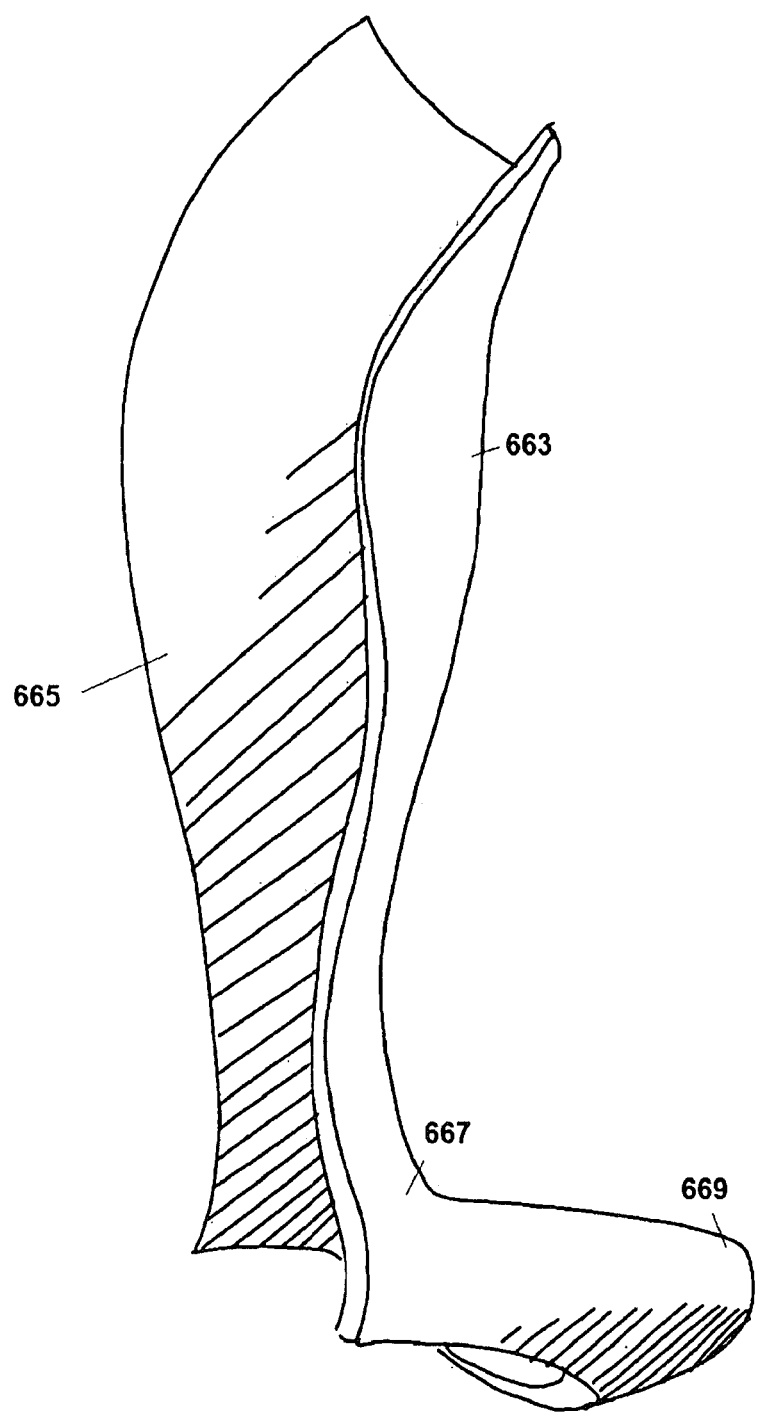
FIG. 14 is a rear view of the prosthetic leg with the shin fairing in place and the calf area exposed.

With reference to FIG. 14, an inner view of a fairing 663 is illustrated that only covers the shin of the prosthetic leg and does not extend above the knee. The fairing 663 was designed to flex at the ankle and attach to the foot portion of the prosthetic leg. The thickness of the fairing 663 can be adjusted by the prosthetic designer. Because a thinner material is more flexible, the areas that are designed to flex may be designed with a thinner wall than the sections of the fairing 663 that do not move. The fairing can be uniform in thickness and both the inner surface and the outer surface of the fairing 453 can correspond to the detected outer surface contours of the patient's intact limb. Similarly, if the fairing is used with a brace embodiment, the inner surface and the outer surface of the fairing 453 can correspond to the detected outer surface contours of the patient's injured limb.

Figure 15:
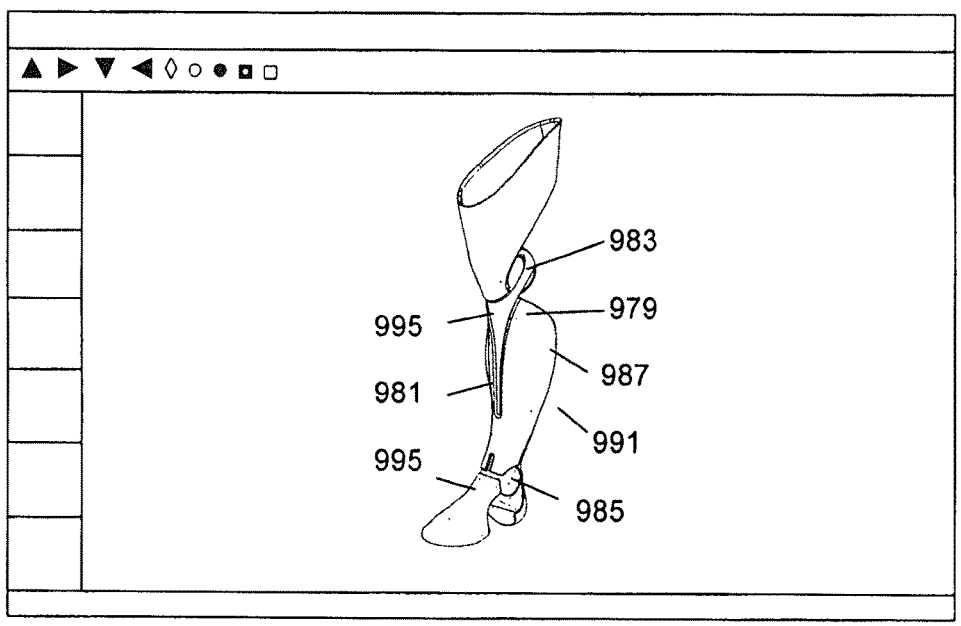
FIG. 15 illustrates a computer screen displaying a prosthetic leg design.

In the previously disclosed embodiments, CAD software has been used to create the framework and fairing that are mounted around an internal load-bearing member. In other embodiments, the outer surface of the leg is bonded to the internal framework and both function as the load-bearing member. With reference to FIG. 15, a prosthetic leg 987 having an external surface 881 that is bonded to an internal framework and function together as the load-bearing member is designed using a CAD program. The prosthetic leg 987 is attached directly to the knee joint 983 and the foot joint 985. In this embodiment, the fairing was designed as a separate component that is placed over the outer surface 981 of the prosthetic leg 989 rather than directly over the framework.

In some cases, the user may wish to alter the design of the leg and fairing so that the prosthetic leg is not an exact replica of the intact leg. Similarly, the brace and fairing can be designed to not exactly match the injured limb. The user may also want to have multiple interchangeable fairings for the prosthetic leg. The prosthetic designer can use the CAD software to modify the original design data for the fairing and the leg or brace so the user can create unique personalized designs. Legs, braces and fairings can be designed to have any desired appearance.

In an embodiment, the CAD system can include a graphical user interface (GUI) that allows the designer to easily change the appearance of the leg, brace and fairing. The GUI can have controls that allow the fairing, brace and leg to be viewed with specific colors, materials, markings and surface features. Within each selected color, the prosthetic designer can also change the appearance by adding color effects such as: opaque, translucent, iridescent and metallic. The GUI can also have controls that allow the leg to be viewed with metal plated sections such as chrome, zinc, gold, silver, nickel and other alloys. A GUI control can also be used to give the surface of the brace or prosthetic leg surface finish. The system can allow the designer to see the prosthetic leg with a flat, matte, gloss, semi-gloss, reflective, brushed, polished, textured or other finish. These modifications can be made to the entire fairing and leg or any exposed portions. The user can select the desired surface appearances that the designer can apply to a virtual brace or leg through the GUI controls. The CAD program will quickly display the virtual brace or prosthetic leg and fairing with all the desired features. The designer and user can check all of the details of the brace or prosthetic design prior to fabrication.

With reference to FIG. 15, an example of a personalized prosthetic leg 987 and fairing 991 design is illustrated. In this example, the prosthetic designer has developed a prosthetic leg 987 which is partially covered with a matte nickel finish 995 that is applied to the outer surface of the leg 987. In this embodiment, the nickel finish 995 is applied to the knee joint 983 and the foot joint 985. In addition to being ornamental, the smooth nickel finish 995 on the knee joint 983 and the foot joint 985 can also provide a smooth sliding surface that improves the movement of the leg 987. The nickel finish 995 is also applied to the center section of the shin and around the top of the leg 987 as an ornamental feature. The prosthetic designer has also used the CAD program to design a black leather fairing 991 that smoothly wraps around most of the leg 987. A similar fairing can be applied to a leg brace.

Figure 16:
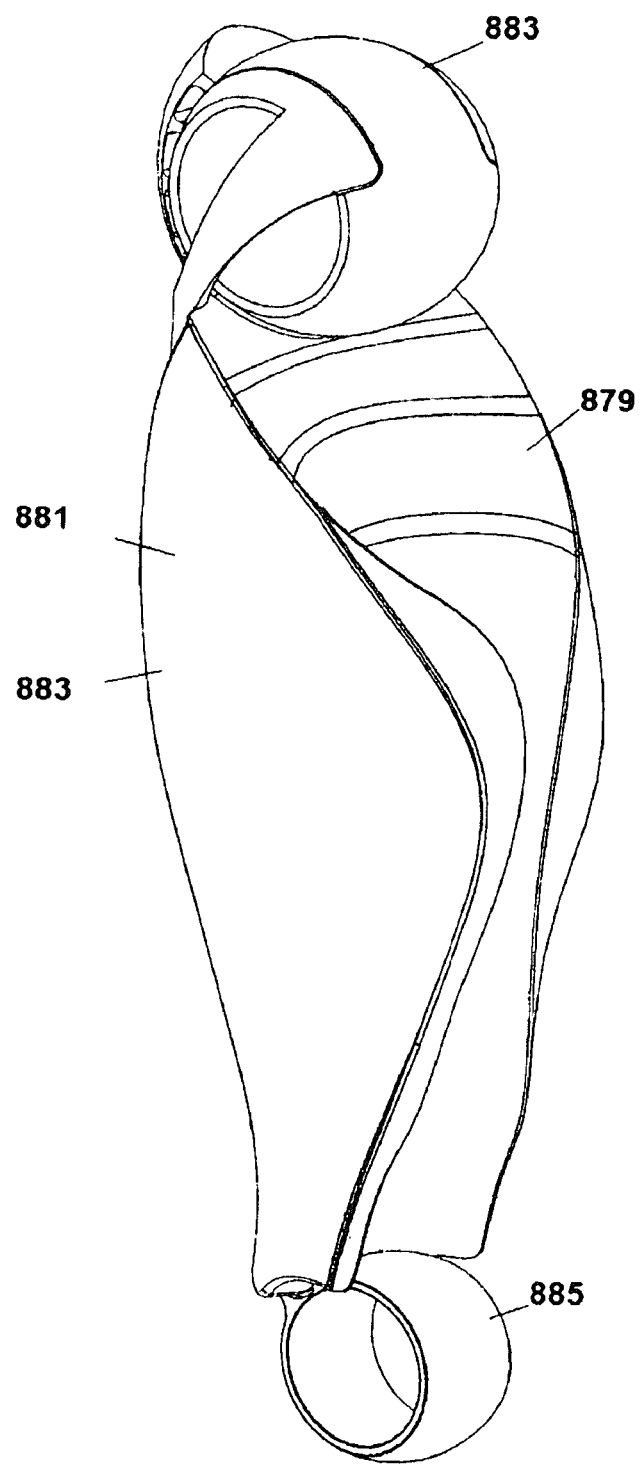
FIG. 16 is a view of a prosthetic leg having a recessed area.

In addition to changing the color and finish of the fairing and surface, the prosthetic designer can also modify the outer surface of the prosthetic limb. With reference to FIG. 16, an example of a surface modification is illustrated. In this example, the prosthetic designer has added a recessed surface 879 in the prosthetic leg 881 that extends along a portion of the calf. FIG. 16 illustrates a cross section of the prosthetic leg 881 that shows the recessed surface 879 as a smooth concave. In other embodiments, the surface of the prosthetic leg can be modified by the prosthetic designer to extend above the mirror image surface.

When the prosthetic designer completes the designs of the prosthetic leg and fairing, the design data produced by the CAD software can be used to custom fabricate the leg and fairing. Rapid prototyping is a general category of systems that uses digital design data and software to fabricate the components from various types of materials including metals, plastics and sand. These machines use an energy beam that is deflected across a bed of liquid or powdered material. The exposure to the energy beam causes the material to fuse together and harden. These fabrication machines are able to create all custom prosthetic limb components.

In order to fabricate the prosthetic leg components with the rapid prototyping machines, the CAD design data must be modified. The normal CAD design data for a component is converted into many parallel cross sections of vector data that extend along the length of the component. The data transmitted between the CAD software and the fabrication machine approximates the shape of component cross sections through many connected triangular facets. Smaller facets produce a higher quality surface but require more time to calculate and can create very larger manufacturing data sets.

The vector data for the component cross sections is read by a rapid prototyping scanner controller that converts the vector data to movement information which is sent to the energy beam scanhead. In a laser beam embodiment, the rapid prototyping machine includes a scanhead having two mirrors that deflect the laser beam in the X and Y coordinates over a bath of material. The fabrication information is then used to control the print head cross section to create each component cross section successively. The scanhead controller reads the fabrication data and causes the print head to expose successive layers of liquid, powder, or sheet material to precise patterns of laser light. Once the layer is completely formed, the component is moved into the bath so a thin layer of the material covers the previously formed layer. The process is repeated many times with new layers formed and fused to the previously formed layers. In an electron beam embodiment, an electron beam is deflected over a bath of material in the X and Y coordinates with magnetic fields. The component cross sections are sequentially formed until the component fabrication is completed.

Figure 17:
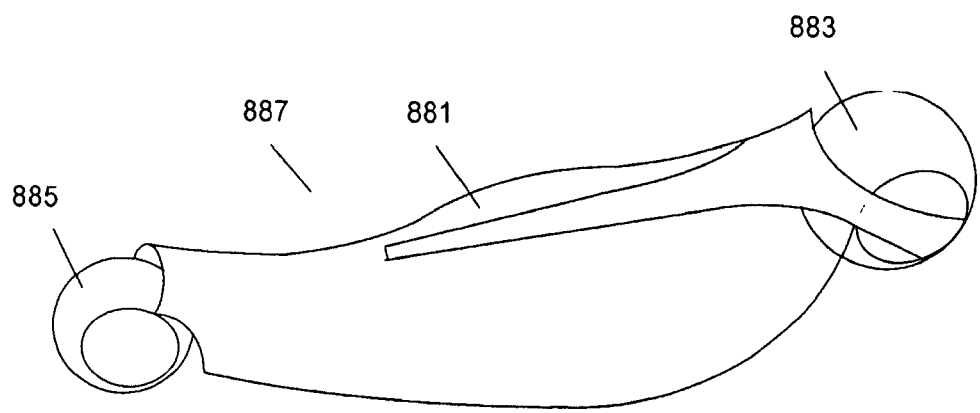
FIGS. 17 and 18 are views of a prosthetic leg having a nickel finish and an attached leather fairing.

The primary advantage to additive fabrication rapid prototyping is the ability to create very complex shapes and geometric features such as the internal framework of the templates and longitudinal members within the prosthetic leg. A light weight and strong prosthetic limb can be made with a rapid prototyping machine from plastic materials such as photopolymers. FIG. 17 illustrates a completed photopolymer leg 887 that was fabricated using a rapid prototyping machine.

The rapid prototyping process can be applied to various materials including thermoplastics, photopolymers, metal powders, eutectic metals, titanium alloys and other materials. Examples of some suitable rapid prototyping machines include: laser sintering machines by EOS GmbH, electron beam sintering machines by A rcam AB and laser stereo lithography machines by 3D Systems Corp. Similar fabrication processes are known by the names: additive manufacturing, rapid manufacturing, layered manufacturing, 3D printing, laser sintering, electron beam melting (EBM), fused material deposition (FDM), etc. All of these fabrication process use a similar operating principle of scanning an energized beam over a bath of material to solidify a precise pattern of the material to form each layer until the entire component is complete.

While rapid prototyping is the preferred fabrication method there are other possible methods for forming the prosthetic limb components. In an embodiment, the design information can be used by a computer numerical control (CNC) which controls a machine tool to fabricate components from a solid block of material by the selective removal of material. A computer controller reads programming instructions and drives a powered mechanical cutting tool. The CNC system numerically directs interpolation of the surface data and controls a cutting tool to create the component. The CNC process is a sculpting process that is much less efficient than the rapid prototyping fabrication process and can produce a substantial amount of scrap material.

The fairing can also be fabricated using the design data. The most appropriate fabrication process may depend upon the fairing material. For example, if the fairing is made from a flexible material, the fairing design data can be used to cut the fairing from flat sheet stock. The fairing design data can be used by a computer controlled machine to precisely cut a sheet of material into the shape of the fairing. The fairing can then be attached directly to a surface of the prosthetic leg with fasteners or an adhesive. If the fairing is made of a more rigid material, the design data can be used to cut the fairing. The fairing can then be bent or molded to form required three-dimensional shape. It is also possible to fabricate a three-dimensional fairing using the described rapid prototyping process. Like the leg component fabrication method described above, the rapid prototyping machine would use the fairing design data to fabricate the fairing from a sequential series of cross section layers.

Another typical requirement of the prosthetic limb is color. The desired color can also be applied to the prosthetic component, brace or fairing during the fabrication process. In an embodiment, the color of the fairing, brace and leg components can be applied through pigments that are mixed with materials used to fabricate the leg. The colors will exist through the structures and cannot be removed. Alternatively, the color may be applied to a leg component or brace in a separate painting, dying, deposition or other coloring process to form a color layer over the outer surfaces of the leg, brace and fairing.

In another embodiment, a metal or ceramic layer can be deposited onto the outer surfaces of the leg, brace and fairing. The method used to deposit the metal layer can depend upon the base material of the leg, brace or fairing. The metal layer can be deposited on a non-conductive plastic component through an electroless or chemical plating process. If the component being plated is a conductive material, an electro-chemical plating process can be used to deposit the metal layer. After the color or metal layers are applied to the prosthetic components, additional surface finishing processes can be performed. Examples of surface finishes include flat, matte, gloss, semi-gloss, reflective, brushed, polished and textured that can be applied through known mechanical or chemical processes. A protective clear plastic or paint coating may also be applied to the leg, brace and fairing.

The last fabrication step can be attaching the fairings to the prosthetic leg or brace. The fairing can be attached in many different ways. As discussed, in the preferred embodiment, the fairing is a removable structure that can be easily replaced by the user. Releasable fasteners can be used to hold the fairing to the member. Examples of releasable fasteners include bolts, buckles, buttons, clamps, clips, pins, retainers, rivets, bands, snaps, stitching, straps, tacks, ties, zippers, etc. The fairing can also be attached to the leg or brace with an adhesive. In an alternative embodiment, the fairing is permanently attached to the leg or brace. Processes that can more permanently attach the fairing to the leg include: soldering, welding, and fusing.

Figure 18:
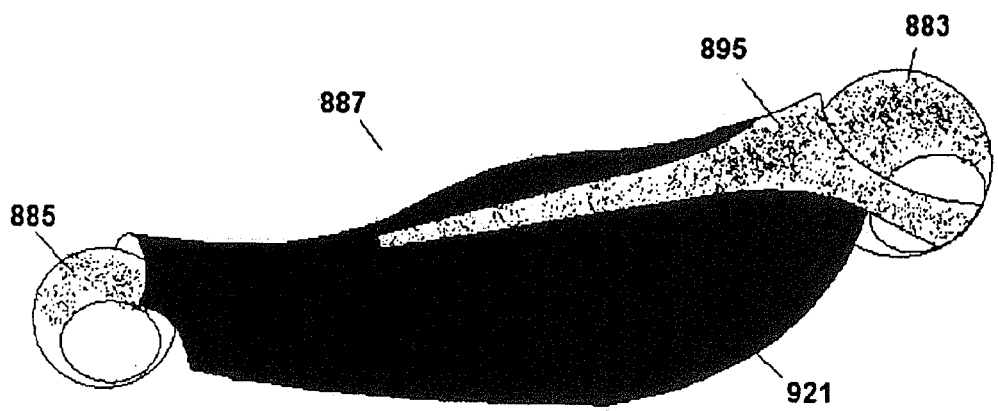

FIG. 18, illustrates a prosthetic leg 887 after the surfaces have been metal plated and the fairing has been attached. The exposed areas of the prosthetic leg 887, the knee joint and ankle joint have a nickel finish 895. The nickel finish was applied over the plastic leg using an electroless nickel-plating process. The fairing 921 was cut from a smooth black leather material and attached to the outer surface of the leg 887 within a recessed area that extends around the shin and calf sections. The leather fairing 921 was attached to the prosthetic leg 887 with an adhesive that allows the fairing 921 to be removed and replaced with another fairing.

Figure 19:
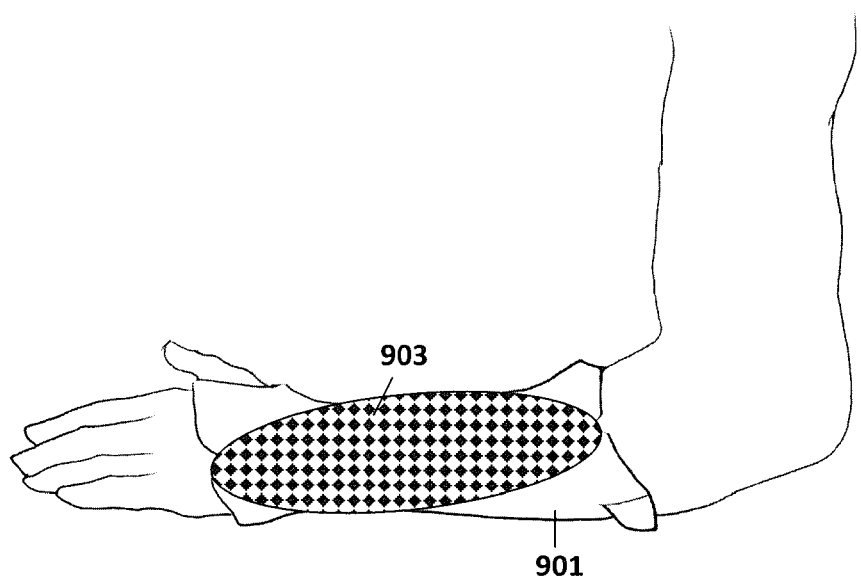
FIG. 19 illustrates an arm brace with a fairing attached to an outer surface.

With reference to FIG. 19, a substantially similar fairing can be attached over a brace such as an arm brace 901. In an embodiment, the interior surface of the arm brace 901 corresponds to the surface topography of the injured arm 905 that was obtained by the described photogrammetry process. The brace 901 can have a uniform thickness. Thus, the outer surface also corresponds to the surface topography of the injured arm. A fairing 903 can be placed around the brace 901. Since the fairing 903 is designed to fit around the brace 901, the inner surface of the fairing 903 that contacts the brace 901 can have contours that match the outer surface of the injured portion of the body. The fairing 903 can include various different materials such as metals, plastics, leather, etc. as described above. In this example, the fairing can be marked with a graphical pattern that is either formed with different colors, materials, holes, etc. The fairing 903 can be attached to the brace 901 with releasable fasteners or an adhesive.

It will be understood that the inventive system has been described with reference to particular embodiments, however additions, deletions and changes could be made to these embodiments without departing from the scope of the inventive system. For example, the same processes described for designing and fabricating a prosthetic leg can also be applied to the design and construction of a prosthetic arm that can include a socket, an elbow, an elongated member and an artificial hand. Although the prosthetic limb has been described that includes various components, it is well understood that these components and the described configuration can be modified and rearranged in various other configurations.

What is claimed is:

1. A method for creating a fairing for a prosthetic limb comprising:
   providing a computing device having a display and a graphical user interface that displays a plurality of colors and a plurality of graphical patterns for the fairing;
   photographing an intact limb of a patient's body with a digital camera to produce a plurality of 2D digital images;
   transmitting photographs of the limb to the computer;
   obtaining surface measurements of the intact limb of the patient's body;
   inputting to the graphical user interface a selected color of the fairing selected from the plurality of colors and a selected graphical pattern selected from the plurality of graphical patterns for the fairing;
   creating a fairing design from the selected color, the selected graphical pattern and the measurements of the limb; and
   fabricating the fairing from the fairing design wherein the fairing has an outer surface that corresponds to the measurements of the intact limb, the fairing is the selected color and the selected graphical pattern, and the fairing includes fastener components for holding the fairing to the prosthetic limb.

2. The method of claim 1 wherein the fabricating of the fairing includes applying a metal layer to an outer surface of the fairing that alters the appearance of the fairing.

3. The method of claim 1 wherein the fabricating of the fairing includes a plurality of selected colors.

4. The method of claim 1 wherein the fabricating of the fairing includes applying a colored dye or paint in an outer surface of the fairing.

5. The method of claim 1 wherein the fabricating of the fairing includes applying a metal layer on an outer surface of the fairing that has a brushed finish, a polished finish or a sand blasted finish.

6. The method of claim 1 wherein the fabricating of the fairing includes applying a leather material on an outer surface of the fairing.

7. The method of claim 1 wherein the selected graphical pattern of the fairing includes a plurality of openings that alter the appearance of the fairing.

8. The method of claim 7 wherein the selected graphical pattern includes a plurality of colors, materials and holes.

9. The method of claim 1 wherein the fairing is discontinuous, the fairing covering a first portion of the prosthetic limb and not covering a second portion of the prosthetic limb.

10. The method of claim 9 wherein the first portion of the fairing is attached to an upper surface of the prosthetic limb and the second portion of the fairing is attached to a lower surface of the prosthetic limb.

11. The method of claim 9 wherein the first portion of the fairing is attached to a front surface of the prosthetic limb and the second portion of the fairing is attached to a rear surface of the prosthetic limb.

12. The method of claim 1 wherein the fabrication of the fairing includes applying a plated section made of: chrome, zinc, gold, silver, or nickel.

13. The method of claim 1 wherein the fabrication of the fairing includes applying a metal material that alters the appearance of the fairing.

14. The method of claim 1 wherein the fairing design includes one or more of the following finishing processes: plating, texturing, brushing, polishing or sand blasting.

15. The method of claim 1 wherein the fairing includes a plurality of different materials.

16. The method of claim 1 wherein the prosthetic limb is a prosthetic leg.

17. A method for creating multiple interchangeable fairings comprising:
provifing a computer having a computer having a display and a graphical user interface that displays a plurality of colors and a plurality of graphical patterns for the fairing;
photographing an intact limb of a patient's body with a digital camera to produce a plurality of 2D digital images;
transmitting photographs of the limb to the computer;
obtaining surface measurements of the limb of the patient's body;
inputting to the graphical user interface a selected color for each of the multiple interchangeable fairings selected from the plurality of colors and a selected graphical pattern selected from the plurality of graphical patterns for each of the interchangeable fairings;
creating fairing design data having an outer surface data that corresponds to the surface data for the intact limb of the body using a computer, wherein the computer includes a graphical user interface that allows colors of the interchangeable fairings to be selected from a plurality of colors and viewed prior to fabrication; and
fabricating the multiple interchangeable fairing from the fairing design wherein the interchangeable fairings have outer surfaces that correspond to the measurements of the limb, each of the multiple interchangeable fairings includes one of the selected colors and one of the selected graphical patterns and the fairings include fastener components for holding the fairing to the prosthetic limb.

18. The method of claim 17 wherein the interchangeable fairing designs each include a plurality of openings that alter the appearances of the interchangeable fairings.

19. The method of claim 17 wherein a plurality of openings form a graphical pattern that alter the appearances of the interchangeable fairings.

20. The method of claim 17 wherein the interchangeable fairing designs cover a first portion of a prosthetic limb and not covering a second portion of the prosthetic limb.

* * * * *